US006407092B1

(12) United States Patent
Hester et al.

(10) Patent No.: US 6,407,092 B1
(45) Date of Patent: Jun. 18, 2002

(54) TETRACYCLIC AZEPINOINDOLE COMPOUNDS

(75) Inventors: Jackson B. Hester, Galesburg; Bruce N. Rogers, Portage; Eric Jon Jacobsen, Kalamazoo; Michael D. Ennis, Portage; Brad A. Acker; Susan L. Vander Velde, both of Kalamazoo; Kristine E. Frank, Portage, all of MI (US)

(73) Assignee: Pharmacia & Upjohn Company, Bridgewater, NJ (US)

( * ) Notice: Subject to any disclaimer, the term of this patent is extended or adjusted under 35 U.S.C. 154(b) by 0 days.

(21) Appl. No.: 09/553,246

(22) Filed: Apr. 20, 2000

Related U.S. Application Data
(60) Provisional application No. 60/130,881, filed on Apr. 23, 1999.

(51) Int. Cl.[7] ................... C07D 471/16; C07D 223/00; C07D 221/00; C07D 498/16; C07D 513/16
(52) U.S. Cl. .................. 514/215; 540/577; 540/578
(58) Field of Search ............................. 540/577, 578; 514/215

(56) References Cited

U.S. PATENT DOCUMENTS

| 3,676,558 A | 7/1972 | Hester, Jr. ................. 424/274 |
| 3,839,357 A | 10/1974 | Hester, Jr. ............. 260/326.5 B |

FOREIGN PATENT DOCUMENTS

| EP | 0377238 | 7/1990 |
| WO | 00/77001 | 12/2000 |
| WO | 00/77002 | 12/2000 |

OTHER PUBLICATIONS

Abstract of WO00/077010, Dec. 2000.*
Abstract of WO00/077002, Dec. 2000.*
Abstract of WO00/077001, Dec. 2000.*
Baxter, G., et al., "5–HT$_2$ receptor subtypes: a family re–united?", *Trends in Pharmacological Reviews*, 16, pp. 105–110, (1995).
Bös, M., et al., "Novel Antagonists of 5HT$_{2C}$ Receptors. Synthesis and Biological Evaluation of Substituted 2–(Indol–1–yl)–1–methylethylamines and 2–(Indeno[1, 2–b]pyrrol–1–yl)–1–methylethylamines. Improved Therapeutics for Obsessive Compulsive Disorder", *Journal of Medicinal Chemistry*, 40 (*17*) , pp. 2762–2769, (Aug. 15, 1997).

Bromidge, S.M., et al., "Novel and Selective 5–HT$_{2C/2B}$ Receptor Antagonists as Potential Anxiolytic Agents: Synthesis, Quantitative Structure–Activity Relationships, and Molecular Modeling of Substituted 1–(3–Pyridylcarbamoyl) indolines", *Journal of Medicinal Chemistry*, 41 (*10*) , pp. 1598–1612, (May 7, 1998).
Dekeyne, A., et al., "Discriminative stimulus properties of the novel serotonin (5–HT)$_{2C}$ receptor agonist, RO 60–0175: a pharmacological analysis", *Neuropharmacology*, 38 (*2*) , pp. 415–423, (Mar. 1999).
Gershon, M.D., et al., "5–Hydroxytryptamine and enteric neurones", *The Peripheral Actions of 5–Hydroxytryptamine*, Chapter 11, Oxford University Press, pp. 247–273, (1989).
Glennon, R.A., "Serotonin Receptors: Clinical Implications", *Neuroscience & Behavioral Reviews*, 14 (*1*) , pp. 35–47, (1990).
Hoyer, D., et al., "VII. International Union of Pharmaclogy Classification of Receptors for 5–Hydroxytryptamine (Serotonin)", *Pharmacological Reviews*, 46 (2), pp. 157–203, (Jun. 1994).
Jenck, F., et al., "The role of 5–HT$_{2C}$ receptors in affective disorders", *Exp. Opin. Invest. Drugs*, 7 (*10*) , pp. 1587–1599, (1998).
Martin, J.R., et al., "5–HT$_{2C}$ Receptor Agonists: Pharmacological Characteristics and Therapeutic Potential", *Journal of Pharmacology and Experimental Therapeutics*, 286 (*2*) , pp. 913–924, (1998).
Saxena, P.R., et al., "Cardiovascular Effects of Serotonin Agonists and Antagonists", *Journal of Cardiovascular Pharmacology*, 15 (*Suppl. 7*) , pp. S17–S34, (1990).

* cited by examiner

*Primary Examiner*—Bruck Kifle
(74) *Attorney, Agent, or Firm*—Schwegman, Lundberg, Woessner & Kluth, P.A.

(57) ABSTRACT

The present invention provides compounds of formula I:

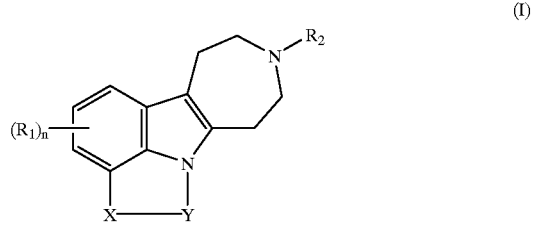

wherein $R_1$, $R_2$, X and Y have any of the values defined in the specification, as well as pharmaceutical compositions comprising the compounds. The invention also provides therapeutic methods as well as processes and intermediates useful for preparing compounds of formula (I).

38 Claims, 6 Drawing Sheets

TETRACYCLIC AZEPINOINDOLE COMPOUNDS

PRIORITY OF INVENTION

This application claims priority from U.S. Provisional Application No. 60/130,881, filed Apr. 23, 1999.

FIELD OF THE INVENTION

The present invention provides tetracyclic 1,2,3,4,5,6-hexahydroazepino-[4,5-b]indole derivatives having a ring connecting position 6 (N-6) and position 7 (C-7), and more specifically, provides compounds of formula (I) described hereinbelow. These compounds are 5-HT ligands, and are useful for treating diseases wherein modulation of 5-HT activity is desired.

BACKGROUND OF THE INVENTION

Serotonin has been implicated in a number of diseases and conditions which originate in the central nervous system. These include diseases and conditions related to sleeping, eating, perceiving pain, controlling body temperature, controlling blood pressure, depression, anxiety, schizophrenia, and other bodily states. R. W. Fuller, Biology of Serotonergic Transmission, 221 (1982); D. J. Boullin, Serotonin in Mental Abnormalities 1:316 (1978); J. Barchas, et al., Serotonin and Behavior, (1973). Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, receptor-specific agonists and antagonists are of interest for the treatment of a wide range of disorders, including anxiety, depression, hypertension, migraine, obesity, compulsive disorders, schizophrenia, autism, neurodegenerative disorders (e.g. Alzheimer's disease, Parkinsonism, and Huntington's chorea), and chemotherapy-induced vomiting. M. D. Gershon, et al., The Peripheral Actions of 5-Hydroxytryptamine, 246 (1989); P. R. Saxena, et al., Journal of Cardiovascular Pharmacology, 15:Supplement 7 (1990).

The major classes of serotonin receptors (5-$HT_{1-7}$) contain fourteen to eighteen separate receptors that have been formally classified. See Glennon, et al., Neuroscience and Behavioral Reviews, 1990, 14, 35; and D. Hoyer, et al. Pharmacol. Rev. 1994, 46, 157–203. Recently discovered information regarding subtype identity, distribution, structure, and function suggests that it is possible to identify novel, subtype specific agents, having improved therapeutic profiles (e.g. fewer side effects).

For example, the 5-$HT_2$ family of receptors is comprised of 5-$HT_{2A}$, 5-$HT_{2B}$, and 5-$HT_{2C}$ subtypes, which have been grouped together on the basis of primary structure, secondary messenger system, and operational profile. All three subtypes are G-protein coupled, activate phospholipase C as a principal transduction mechanism, and contain a seven-transmembrane domain structure. There are distinct differences in the distribution of the three 5-$HT_2$ subtypes. The 5-$HT_{2B}$ and 5-$HT_{2A}$ receptors are widely distributed in the periphery, while the 5-$HT_{2C}$ receptor has been found only in the central nervous system, being highly expressed in many regions of the human brain. See G. Baxter, et al. Trends in Pharmacol. Sci. 1995, 16, 105–110.

Subtype 5-$HT_{2A}$ has been associated with effects including vasoconstriction, platelet aggregation, and bronchoconstriction, while subtype 5-$HT_{2C}$ has been associated with diseases that include depression, anxiety, obsessive compulsive disorder, panic disorders, phobias, psychiatric syndromes, and obesity. Very little is known about the pharmacologic role of the 5-$HT_{2B}$ receptor. See F. Jenck, et al., Exp. Opin. Invest. Drugs, 1998, 7, 1587–1599; M. Bos, et al., J. Med. Chem., 1997, 40, 2762–2769; J. R. Martin, et al., The Journal of Pharmacology and Experimental Therapeutics, 1998, 286, 913–924; S. M. Bromidge, et al., J. Med. Chem., 1998, 41, 1598–1612; G. A. Kennett, Drugs, 1998, 1, 4, 456–470; and A. Dekeyne, et al., Neuropharmacology, 1999, 38, 415–423.

U.S. Pat. No. 3,676,558, issued Jul. 11, 1972, discloses compositions comprising specific 6-alkyl-1,2,3,4,5,6-hexahydroazepino[4,5-b]indole compounds. The compositions are reported to be useful to suppress hunger in mammals. This patent also discloses a method for inducing anorexia in obese subjects to produce weight loss. The azepino[4,5-b]indole compounds disclosed in this patent lack the ring connecting the 6-position and the 7-position that is present in the compounds of the instant invention.

U.S. Pat. No. 3,839,357, issued Oct. 1, 1974, discloses specific 1,2,3,4,5,6-hexahydroazepino[4,5-b]indole compounds, which are reported to have sedative or tranquilizing action. The azepino[4,5-b]indole compounds disclosed in this patent also lack the ring connecting the 6-position and the 7-position that is present in the compounds of the instant invention.

There is currently a need for pharmaceutical agents that are useful to treat diseases and conditions that are associated with 5-HT receptors.

SUMMARY OF THE INVENTION

In accordance with the present invention, novel compounds which demonstrate useful biological activity, and particularly activity as 5-HT receptor ligands, are provided. Thus, the present invention provides a compound of formula I:

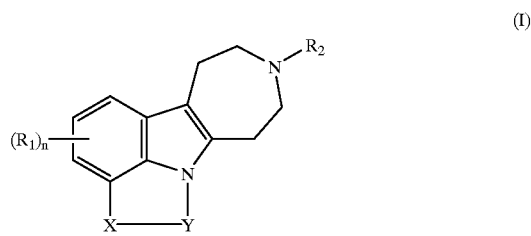

(I)

wherein, each $R_1$ is independently hydroxy, nitro, halo, cyano, trifluoromethyl, trifluoromethoxy, $C_{1-7}$alkyl, $C_{1-7}$alkoxy, $C_{1-7}$alkanoyl, $C_{1-7}$alkoxycarbonyl, $C_{1-7}$alkanoyloxy, aryl, heteroaryl, —S(O)$_m$NR$_a$R$_b$, NR$_c$R$_d$, —S(O)$_m$R$_e$, or —C(=O)NR$_a$R$_b$, wherein any $C_{1-7}$alkyl, $C_{1-7}$alkoxy, $C_{1-7}$alkanoyl, $C_{1-7}$alkoxycarbonyl, or $C_{1-7}$alkanoyloxy of $R_1$ is optionally partially unsaturated and is optionally substituted with aryl, aryloxy, heteroaryl, heteroaryloxy, hydroxy, nitro, halo, cyano, $C_{1-7}$alkoxy, $C_{1-7}$alkanoyl, $C_{1-7}$alkoxycarbonyl, $C_{1-7}$alkanoyloxy, —S(O)$_m$R$_e$, —S(O)$_m$NR$_a$R$_b$, NR$_c$R$_d$, or —C(=O)NR$_a$R$_b$;

$R_2$ is hydrogen, $C_{1-7}$alkyl, $C_{1-7}$alkanoyl, arylcarbonyl, aryl, (aryl)$C_{1-7}$alkyl, $C_{1-7}$alkoxycarbonyl, aryloxycarbonyl, arylsulfonyl, or (aryl)$C_{1-7}$ alkoxycarbonyl;

X and Y together are a 2, 3, or 4 membered saturated or partially unsaturated chain comprising one or more carbon atoms and optionally comprising one oxy (—O—), thio (—S—), sulfinyl (—SO—), sulfonyl (S(O)$_2$—), or NR$_f$ in the chain; wherein the chain is optionally substituted on each carbon with oxo (=O), thioxo (=S), —NR$_q$R$_r$, —S(O)$_p$R$_s$, or —OR$_t$, or with one or two substituents independently selected from the group consisting of C$_{1-7}$alkyl, (C$_{1-7}$alkoxy)C$_{1-7}$alkyl, aryl, (aryl)C$_{1-7}$alkyl, heteroaryl, (heteroaryl)C$_{1-7}$alkyl, and (aryl)oxyC$_{1-7}$alkyl; or wherein the chain is optionally substituted on a carbon with a 4, 5, or 6 membered spirocyclic carbon ring; or wherein the chain is optionally substituted on two adjacent atoms with a 2, 3, or 4 membered alkylene chain (e.g. —CH$_2$CH$_2$—, —CH$_2$CH$_2$CH$_2$—, or —CH$_2$CH$_2$CH$_2$CH$_2$—) forming a ring that is fused to the ring comprising X and Y;

each m is independently 0, 1, or 2;

n is 0, 1, 2, or 3;

p is 0, 1, or 2;

each R$_a$ and R$_b$ is independently hydrogen, C$_{1-7}$alkyl, aryl, (aryl)C$_{1-7}$alkyl, heteroaryl, or (heteroaryl)C$_{1-7}$alkyl; or R$_a$ and R$_b$ together with the nitrogen to which they are attached form a pyrrolidino, piperidino, morpholino, or thiomorpholino ring;

each R$_c$ and R$_d$ is independently hydrogen, C$_{1-7}$alkyl, C$_{1-7}$alkanoyl, C$_{1-7}$alkoxycarbonyl, aryl, (aryl)C$_{1-7}$alkyl, heteroaryl, (heteroaryl)C$_{1-7}$alkyl, arylcarbonyl, heteroarylcarbonyl, aryloxycarbonyl, or heteroaryloxycarbonyl; or R$_c$ and R$_d$ together with the nitrogen to which they are attached form a pyrrolidino, piperidino, morpholino, or thiomorpholino ring;

each R$_e$ is independently hydrogen, C$_{1-7}$alkyl, aryl, (aryl)C$_{1-7}$alkyl, heteroaryl, or (heteroaryl)C$_{1-7}$alkyl;

R$_f$ is hydrogen, C$_{1-7}$alkyl, aryl, (aryl)C$_{1-7}$alkyl, heteroaryl, (heteroaryl)C$_{1-7}$alkyl, or is a bond to a 2, 3, or 4 membered alkylene chain that forms a ring that is fused to the ring comprising X and Y;

each R$_q$ and R$_r$ is independently hydrogen, C$_{1-7}$alkyl, aryl, (aryl)C$_{1-7}$alkyl, heteroaryl, or (heteroaryl)C$_{1-7}$alkyl; or R$_q$ and R$_r$ together with the nitrogen to which they are attached form a pyrrolidino, piperidino, morpholino, or thiomorpholino ring;

R$_s$ is C$_{1-7}$alkyl, aryl, (aryl)C$_{1-7}$alkyl, heteroaryl, or (heteroaryl)C$_{1-7}$alkyl; and R$_t$ is hydrogen, C$_{1-7}$alkyl, aryl, (aryl)C$_{1-7}$alkyl, heteroaryl, or (heteroaryl)C$_{1-7}$alkyl;

wherein any aryl or heteroaryl ring of R$_1$, R$_2$, X, Y, R$_a$–R$_f$, or R$_q$–R$_t$ is optionally substituted with one or more (e.g. 1, 2, 3, or 4) substituents independently selected from halo, hydroxy, cyano, nitro, trifluoromethyl, trifluoromethoxy, C$_{1-7}$alkyl, C$_{1-7}$alkoxy, phenyl, sulfonyl, NR$_j$R$_k$, or —C(=O)NR$_j$R$_k$; wherein each R$_j$ and R$_k$ is independently hydrogen, C$_{1-7}$alkyl, C$_{1-7}$alkanoyl, C$_{1-7}$alkoxycarbonyl, aryl, (aryl)C$_{1-7}$alkyl, arylcarbonyl, or aryloxycarbonyl; or R$_j$ and R$_k$ together with the nitrogen to which they are attached form a pyrrolidino, piperidino, morpholino, or thiomorpholino ring;

or a pharmaceutically acceptable salt thereof;

provided Y is not oxy, thio, sulfinyl, or NR$_f$; and provided X and Y together are not a 2-membered unsaturated chain; and provided no carbon of X and Y is bonded to more than one oxy, thio, sulfinyl, or NR$_f$.

In another aspect, the present invention also provides:

a pharmaceutical composition comprising a compound of formula I, or a pharmaceutically acceptable salt thereof, and a pharmaceutically acceptable excipient (the composition preferably comprises a therapeutically effective amount of the compound or salt), a method for treating a disease or condition in a mammal (e.g. a human) wherein a 5-HT receptor is implicated and modulation of a 5-HT function is desired comprising administering a therapeutically effective amount of a compound of formula I, or a pharmaceutically acceptable salt thereof to the mammal, a method for treating or preventing a disease or disorder of the central nervous system in a mammal comprising administering a therapeutically effective amount of a compound of formula I, or a pharmaceutically acceptable salt thereof to the mammal, and a method for modulating 5-HT receptor function, comprising administering an effective modulatory amount of a compound of formula I, or a pharmaceutically acceptable salt thereof.

The invention also provides novel intermediates and processes disclosed herein that are useful for preparing compounds of formula I.

DETAILED DESCRIPTION OF THE INVENTION

Figure 1:
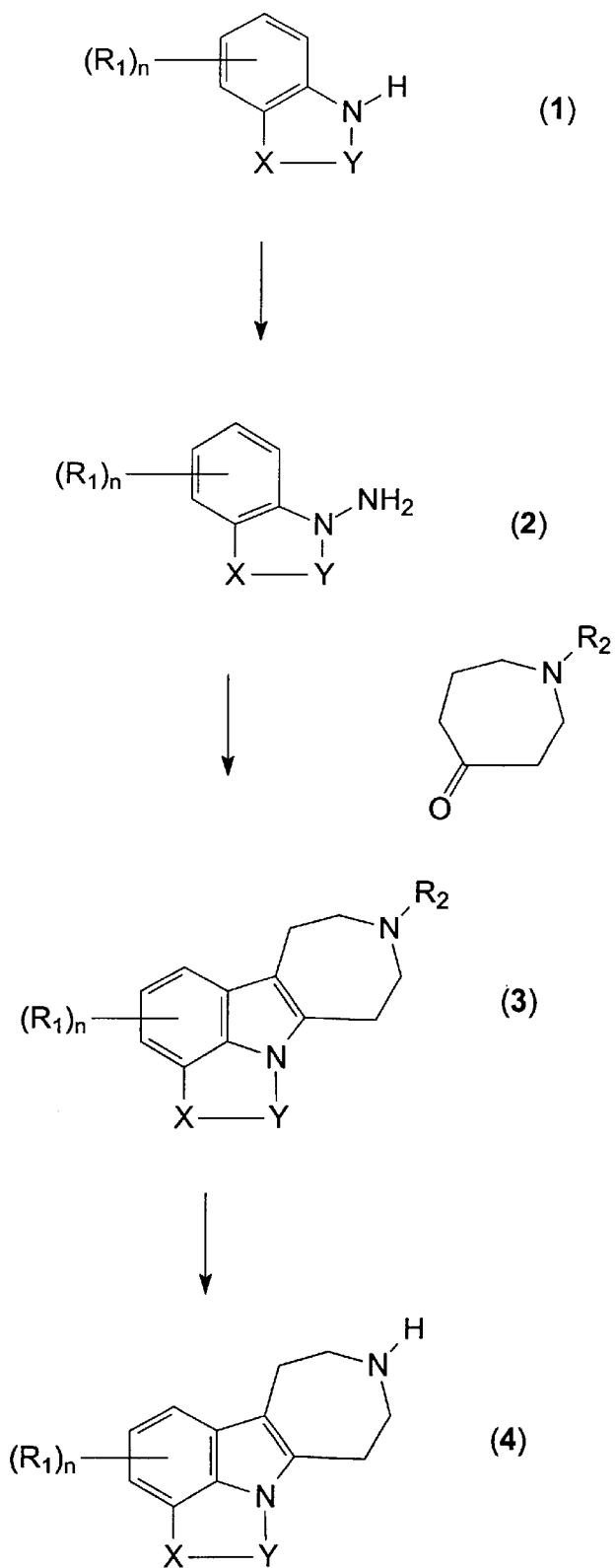
FIGS. 1–6 illustrate synthetic processes and intermediates useful for preparing compounds of the invention.
Figure 2:
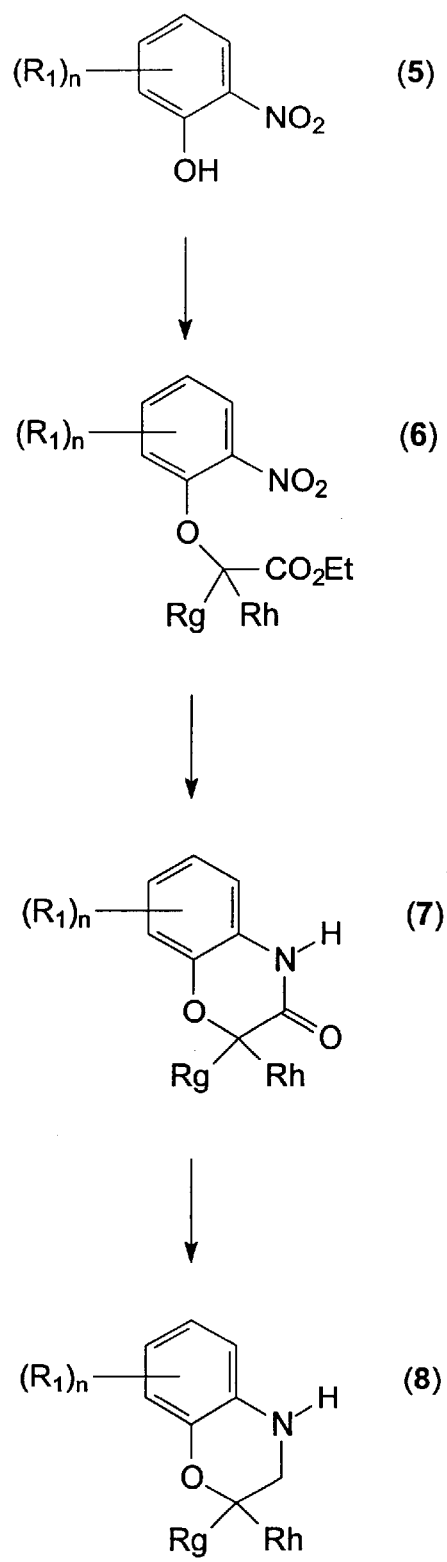

The compounds of the invention are useful for treating or preventing diseases or disorders of the central nervous system. Specific diseases or disorders of the central nervous system for which a compound of formula I may have activity include, but are not limited to: obesity, depression, schizophrenia, schizophreniform disorder, schizoaffective disorder, delusional disorder, a stress related disease (e.g. general anxiety disorder), panic disorder, a phobia, obsessive compulsive disorder, post-traumatic-stress syndrome, immune system depression, a stress induced problem with the urinary, gastrointestinal or cardiovascular system (e.g., stress incontinence), neurodegenerative disorders, autism, chemotherapy-induced vomiting, hypertension, migraine, headaches, cluster headaches, sexual dysfunction in a mammal (e.g. a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition (e.g., dementia, mental retardation or delirium)), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders, psychotic disorder due to medical condition, psychotic disorder NOS), mood disorder (major depressive or bipolar disorder with psychotic features) seasonal affective disorder, a sleep disorder, a specific development disorder, agitation disorder, selective serotonin reuptake inhibition (SSRI) "poop out" syndrome or a Tic disorder (e.g., Tourette's syndrome).

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically-active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine 5-HT activity using the standard tests which are well known in the art.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

Specifically, $C_{1-7}$alkyl can be methyl, ethyl, propyl, isopropyl, butyl, iso-butyl, sec-butyl, pentyl, 3-pentyl, hexyl, or heptyl; $C_{1-7}$alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; $C_{1-7}$alkanoyl can be acetyl, propanoyl, butanoyl, pentanoyl, 4-methylpentanoyl, hexanoyl, or heptanoyl; $C_{1-7}$alkoxycarbonyl can be methoxycarbonyl, ethoxycarbonyl, propoxycarbonyl, isopropoxycarbonyl, butoxycarbonyl, pentoxycarbonyl, hexyloxycarbonyl, or heptyloxycarbonyl; $C_{1-7}$alkanoyloxy can be acetoxy, propanoyloxy, butanoyloxy, isobutanoyloxy, pentanoyloxy, hexanoyloxy, or heptanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_1$ is hydroxy, nitro, halo, cyano, trifluoromethyl, trifluoromethoxy, $C_{1-7}$alkyl, $C_{1-7}$alkoxy, $C_{1-7}$alkanoyl, $C_{1-7}$alkoxycarbonyl, $C_{1-7}$alkanoyloxy, aryl, heteroaryl, —S(O)$_m$NR$_a$R$_b$, NR$_c$R$_d$, —S(O)$_m$R$_e$, or —C(=O)NR$_a$R$_b$, wherein any $C_{1-7}$alkyl, $C_{1-7}$alkoxy, $C_{1-7}$alkanoyl, $C_{1-7}$alkoxycarbonyl, or $C_{1-7}$alkanoyloxy of $R_1$ is optionally substituted with aryl, aryloxy, heteroaryl, heteroaryloxy, hydroxy, nitro, halo, cyano, $C_{1-7}$alkoxy, $C_{1-7}$alkanoyl, $C_{1-7}$alkoxycarbonyl, $C_{1-7}$alkanoyloxy, —S(O)$_m$ R$_e$, —S(O)$_m$NR$_a$R$_b$, NR$_c$R$_d$, or —C(=O)NR$_a$R$_b$.

A specific value for $R_1$ is hydroxy, nitro, halo, cyano, trifluoromethyl, trifluoromethoxy, $C_{1-7}$alkyl, $C_{1-7}$alkoxy, $C_{1-7}$alkanoyl, $C_{1-7}$alkoxycarbonyl, $C_{1-7}$alkanoyloxy, aryl, heteroaryl, —S(O)$_m$NR$_a$R$_b$, NR$_c$R$_d$, —S(O)$_m$R$_e$, or —C(=O)NR$_a$R$_b$, wherein any $C_{1-7}$alkyl or $C_{1-7}$alkoxy of $R_1$ is optionally substituted with aryl, aryloxy, heteroaryl, heteroaryloxy, hydroxy, nitro, halo, cyano, $C_{1-7}$alkoxy, $C_{1-7}$alkanoyl, $C_{1-7}$alkoxycarbonyl, $C_{1-7}$alkanoyloxy, —S(O)$_m$ R$_e$, —S(O)$_m$NR$_a$R$_b$, NR$_c$R$_d$, or —C(=O)NR$_a$R$_b$.

A specific value for $R_1$ is hydroxy, nitro, halo, cyano, trifluoromethyl, trifluoromethoxy, $C_{1-7}$alkyl, $C_{1-7}$alkoxy, $C_{1-7}$alkanoyl, $C_{1-7}$alkoxycarbonyl, $C_{1-7}$alkanoyloxy, aryl, heteroaryl, —S(O)$_m$NR$_a$R$_b$, NR$_c$R$_d$, —S(O)$_m$R$_e$, or —C(=O)NR$_a$R$_b$, wherein any $C_{1-7}$alkyl is optionally substituted with aryl, aryloxy, heteroaryl, heteroaryloxy, hydroxy, nitro, halo, cyano, $C_{1-7}$alkoxy, $C_{1-7}$alkanoyl, $C_{1-7}$alkoxycarbonyl, $C_{1-7}$alkanoyloxy, —S(O)$_m$R$_e$, —S(O)$_m$NR$_a$R$_b$, NR$_c$R$_d$, or C(=O)NR$_a$R$_b$.

A specific value for $R_1$ is hydroxy, nitro, halo, cyano, trifluoromethyl, trifluoromethoxy, $C_{1-7}$alkyl, $C_{1-7}$alkoxy, $C_{1-7}$alkanoyl, $C_{1-7}$alkoxycarbonyl, $C_{1-7}$alkanoyloxy, aryl, heteroaryl, —S(O)$_m$NR$_a$R$_b$, NR$_c$R$_d$, —S(O)$_m$R$_e$, or C(=O)NR$_a$R$_b$.

A specific value for $R_1$ is independently $C_{1-7}$alkyl, $C_{1-7}$alkoxy, trifluoromethyl, or halo.

A specific value for $R_2$ is hydrogen.

A specific value for $R_2$ is $C_{1-4}$alkyl, $C_{1-4}$alkanoyl, arylcarbonyl, (aryl)$C_{1-2}$alkyl, $C_{1-4}$alkoxycarbonyl, aryloxycarbonyl, arylsulfonyl, or (aryl)methoxycarbonyl, wherein any aryl is optionally substituted with 1, 2, or 3 substituents independently selected from $C_{1-4}$alkyl and trifluoromethyl.

A specific value for $R_2$ is methyl, ethyl, propyl, isopropyl, acetyl, tert-butoxycarbonyl, benzyloxycarbonyl, benzyl, or p-toluenesulfonyl.

A specific value for n is 1, 2, or 3.

A specific value for n is 0.

A specific group of compounds are compounds of formula (I) wherein n is 0. It will be clear to one skilled in the art that when n is 0, the benz ring of the indole in formula (I) is substituted with hydrogens.

A specific group of compounds are compounds of formula I wherein X and Y together are a 2, 3, or 4 membered saturated or partially unsaturated chain comprising one or more carbon atoms and optionally comprising one oxy (—O—), thio (—S—), sulfinyl (—SO—), sulfonyl (S(O)$_2$—), or NR$_f$ in the chain; wherein the chain is optionally substituted on each carbon with oxo (=O), thioxo (=S), —NR$_q$R$_r$, —S(O)$_p$R$_s$, or —OR$_t$, or with one or two substituents independently selected from the group consisting of C$_{1-7}$alkyl, (C$_{1-7}$alkoxy)C$_{1-7}$alkyl, aryl, (aryl)C$_{1-7}$alkyl, heteroaryl, (heteroaryl)C$_{1-7}$alkyl, and (aryl)oxyC$_{1-7}$alkyl.

A specific group of compounds are compounds of formula I wherein X and Y together are a 2, 3, or 4 membered saturated or partially unsaturated chain comprising one or more carbon atoms and optionally comprising one oxy (—O—), thio (—S—), sulfinyl (—SO—), sulfonyl (S(O)$_2$—), or NR$_f$ in the chain; wherein the chain is optionally substituted on each carbon with oxo (=O), thioxo (=S), —NR$_q$R$_r$, —S(O)$_p$R$_s$, or —OR$_t$.

A specific group of compounds are compounds of formula I wherein X and Y together are a 2, 3, or 4 membered saturated or partially unsaturated chain comprising one or more carbon atoms and optionally comprising one oxy (—O—), thio (—S—), sulfinyl (—SO—), sulfonyl (S(O)$_2$—), or NR$_f$ in the chain; wherein the chain is optionally substituted on each carbon with one or two substituents independently selected from the group consisting of C$_{1-7}$alkyl, (C$_{1-7}$alkoxy)C$_{1-7}$alkyl, aryl, (aryl)C$_{1-7}$alkyl, heteroaryl, (heteroaryl)C$_{1-7}$alkyl, and (aryl)oxyC$_{1-7}$alkyl.

A specific group of compounds are compounds of formula I wherein X and Y together are a 2, 3, or 4 membered chain comprising one or more carbon atoms and optionally comprising one oxy (—O—), thio (—S—), sulfinyl (—SO—), sulfonyl (S(O)$_2$—), or NR$_f$ in the chain; wherein the chain is optionally substituted on each carbon with oxo (=O), hydroxy, or C$_{1-7}$alkoxy, or with one or two substituents independently selected from the group consisting of C$_{1-7}$alkyl, (C$_{1-7}$alkoxy)C$_{1-7}$alkyl, aryl, (aryl)C$_{1-7}$alkyl, heteroaryl, (heteroaryl)C$_{1-7}$alkyl and (aryl)oxyC$_{1-7}$alkyl; and wherein the chain is optionally substituted on two adjacent atoms with a 2, 3, or 4 membered alkylene chain forming a ring that is fused to the ring comprising X and Y.

A specific group of compounds are compounds of formula I wherein X and Y together are a 2, 3, or 4 membered chain comprising one or more carbon atoms and optionally comprising one oxy (—O—), thio (—S—), sulfinyl (—SO—), sulfonyl (S(O)$_2$—), or NR$_f$ in the chain; wherein the chain is optionally substituted on each carbon with oxo (=O), hydroxy, (aryl)oxy, heteroaryl(oxy), or C$_{1-7}$alkoxy, or with one or two substituents independently selected from the group consisting of C$_{1-7}$alkyl, (C$_{1-7}$alkoxy)C$_{1-7}$alkyl, aryl, (aryl)C$_{1-7}$alkyl, heteroaryl, (heteroaryl)C$_{1-7}$alkyl, and (aryl)oxyC$_{1-7}$alkyl; and wherein the chain is optionally substituted on two adjacent atoms with a 2, 3, or 4 membered alkylene chain forming a ring that is fused to the ring comprising X and Y.

A specific group of compounds are compounds of formula I wherein X and Y together are a 2, 3, or 4 membered carbon chain wherein the chain is optionally substituted on each carbon with oxo (=O), hydroxy, or C$_{1-7}$alkoxy, or with one or two substituents independently selected from the group consisting of C$_{1-7}$alkyl, (C$_{1-7}$alkoxy)C$_{1-7}$alkyl, aryl, (aryl)C$_{1-7}$alkyl, heteroaryl, (heteroaryl)C$_{1-7}$alkyl and (aryl)oxyC$_{1-7}$ alkyl.

A specific group of compounds are compounds of formula I wherein X and Y together are a 2, 3, or 4 membered carbon chain wherein the chain is optionally substituted on each carbon with oxo (=O), hydroxy, (aryl)oxy, heteroaryl(oxy) or C$_{1-7}$alkoxy, or with one or two substituents independently selected from the group consisting of C$_{1-7}$alkyl, (C$_{1-7}$alkoxy)C$_{1-7}$alkyl, aryl, (aryl)C$_{1-7}$alkyl, heteroaryl, (heteroaryl)C$_{1-7}$alkyl, and (aryl)oxyC$_{1-7}$alkyl.

A specific group of compounds are compounds of formula I wherein X and Y together are a 2 or 3 membered carbon chain optionally substituted on each carbon with oxo or hydroxy, or with one or two C$_{1-7}$alkyl.

A specific group of compounds are compounds of formula I wherein X is —O—, —S—, or —C(R$_g$)(R$_h$)—, wherein R$_g$ and R$_h$ are each independently hydrogen, C$_{1-7}$alkyl, (C$_{1-7}$alkoxy)C$_{1-7}$alkyl, aryl, (aryl)C$_{1-7}$alkyl, heteroaryl, (heteroaryl)C$_{1-7}$alkyl or (aryl)oxyC$_{1-7}$alkyl, or R$_g$ and R$_h$ together are oxo.

A specific group of compounds are compounds of formula I wherein Y is —C(R$_g$)(R$_h$)—, —C(R$_g$)(R$_h$)C(R$_g$)(R$_h$)—, —C(R$_g$)(R$_h$)C(R$_g$)(R$_h$)C(R$_g$)(R$_h$)—, —C(R$_g$)(R$_h$)C(=O)—, —C(R$_g$)(R$_h$)C(R$_g$)(R$_h$)C(=O)—, —C(=O)C(R$_g$)(R$_h$)—, or —C(=O)C(R$_g$)(R$_h$)C(R$_g$)(R$_h$)—, and each R$_g$ and R$_h$ is independently hydrogen or C$_{1-7}$alkyl.

A specific group of compounds are compounds wherein X is —O—, —S—, or —C(R$_g$)(R$_h$)—; and Y is —C(R$_g$)(R$_h$)C(=O)—, or —C(R$_g$)(R$_h$)C(R$_g$)(R$_h$)—, wherein each R$_g$ and R$_h$ is independently hydrogen or C$_{1-7}$alkyl.

A specific group of compounds are compounds wherein X is —O— or —S—; and Y is —C(R$_g$)(R$_h$)C(=O)—, —C(=O)C(R$_g$)(R$_h$)—, or —C(R$_g$)(R$_h$)C(R$_g$)(R$_h$)—, wherein each R$_g$ and R$_h$ is independently hydrogen or C$_{1-7}$alkyl.

A specific group of compounds are compounds wherein X and Y together are —CH(R$_g$)CH(R$_g$)—, —CH(R$_g$)CH(R$_g$)CH(R$_g$)—, —CH(R$_g$)CH(R$_g$)CH(R$_g$)CH(R$_g$)—, —C(R$_g$)=C(R$_g$)CH(R$_g$)—, —C(R$_g$)=C(R$_g$)CH(R$_g$)CH(R$_g$)—, —CH(R$_g$)C(R$_g$)=C(R$_g$)CH(R$_g$)—, —O—CH(R$_g$)CH(R$_g$)—, —O—CH(R$_g$)CH(R$_g$)CH(R$_g$)—, —S—CH(R$_g$)CH(R$_g$)—, —S—CH(R$_g$)CH(R$_g$)CH(R$_g$)—, —S(O)—CH(R$_g$)CH(R$_g$)—, —S(O)—CH(R$_g$)CH(R$_g$)CH(R$_g$)—, —S(O)$_2$—CH(R$_g$)CH(R$_g$)—, —S(O)$_2$—CH(R$_g$)CH(R$_g$)CH(R$_g$)—, —NR$_f$—CH(R$_g$)CH(R$_g$)—, —NR$_f$—CH(R$_g$)CH(R$_g$)CH(R$_g$)—, —CH(R$_g$)C(=O)—, —CH(R$_g$)CH(R$_g$)C(=O)—, —CH(R$_g$)CH(R$_g$)CH(R$_g$)C(=O)—, —CH(R$_g$)OC(=O)—, —CH(R$_g$)CH(R$_g$)OC(=O)—, —OCH(R$_g$)C(=O)—, or —OCH(R$_g$)CH(R$_g$)C(=O)—; wherein each R$_g$ is independently hydrogen, C$_{1-7}$alkyl, aryl, (aryl)C$_{1-7}$alkyl or (aryl)oxyC$_{1-7}$alkyl.

A specific group of compounds are compounds wherein X and Y together are —CH(R$_g$)CH$_2$—, —CH(R$_g$)CH(R$_g$)CH$_2$—, —CH(R$_g$)CH(R$_g$)CH(R$_g$)CH$_2$—, —CH=CHCH$_2$—, —CH=CHCH(R$_g$)CH$_2$—, —CH(R$_g$)CH=CHCH$_2$—, —O—CH$_2$CH$_2$—, —O—CH$_2$CH(R$_g$)CH$_2$—, —S—CH$_2$CH$_2$—, —S—CH$_2$CH(R$_g$)CH$_2$—, —S(O)—CH$_2$CH$_2$—, —S(O)—CH$_2$CH(R$_g$)CH$_2$—, —S(O)$_2$—CH$_2$CH$_2$—, —S(O)$_2$—CH$_2$CH(R$_g$)CH$_2$—, —NR$_f$—CH$_2$CH$_2$—, —NR$_f$—CH$_2$CH(R$_g$)CH$_2$—, —CH$_2$C(=O)—, —CH(R$_g$)CH$_2$C(=O)—, —CH(R$_g$)CH(R$_g$)CH$_2$C(=O)—, —CH$_2$OC(=O)—, —CH(R$_g$)CH$_2$OC(=O)—, —OCH$_2$C(=O)—, or —OCH$_2$CH$_2$C(=O)—; wherein each R$_g$ is independently NR$_q$R$_r$, —S(O)$_p$R$_s$, or —OR$_t$.

A specific group of compounds are compounds wherein X and Y together are —CH(R$_g$)CH(R$_g$)—, —CH(R$_g$)CH(R$_g$)CH(R$_g$)—, —C(R$_g$)=C(R$_g$)CH(R$_g$)—, —O—CH(R$_g$)CH(R$_g$)—, —S—CH(R$_g$)CH(R$_g$)—, —S(O)—CH(R$_g$)CH(R$_g$)—, —S(O)$_2$—CH(R$_g$)CH(R$_g$)—, —NR$_f$—CH(R$_g$)CH(R$_g$)—, —CH(R$_g$)C(=O)—, —CH(R$_g$)CH(R$_g$)C(=O)—, —CH(R$_g$)OC(=O)—, —OCH(R$_g$C(=O)—; wherein each R$_g$ is independently hydrogen or C$_{1-7}$alkyl.

A specific group of compounds are compounds wherein X and Y together are —CH(R$_g$)CH(R$_g$)—, —CH(R$_g$)CH(R$_g$)CH(R$_g$)—, —C(R$_g$)=C(R$_g$)CH(R$_g$)—, —O—CH(R$_g$)CH(R$_g$)—, —S—CH(R$_g$)CH(R$_g$)—, —S(O)—CH(R$_g$)CH(R$_g$)—, —S(O)$_2$—CH(R$_g$)CH(R$_g$)—, —NR$_f$—CH(R$_g$)CH(R$_g$)—, or —CH(R$_g$)CH(R$_g$)C(=O)—; wherein each R$_g$ is independently hydrogen, C$_{1-7}$alkyl, or together with an R$_g$ on an adjacent carbon atom forms a fused 4, 5, or 6, membered carbocyclic ring.

A specific group of compounds are compounds wherein X and Y together are —CH($R_g$)CH($R_g$)—, —CH($R_g$)CH($R_g$)CH($R_g$)—, —O—CH($R_g$)CH($R_g$)—, —S—CH($R_g$)CH($R_g$)—; wherein each $R_g$ is independently hydrogen, $C_{1-7}$alkyl, aryl, or (aryl)$C_{1-7}$alkyl.

A specific group of compounds are compounds wherein X and Y together are —$CH_2CH_2CH_2$—, —$CH_2CH_2C(CH_3)$H—, —$CH_2C(CH_3)HCH_2$—, —$C(CH_3)HCH_2CH_2$—, —$CH_2CH_2$—, —$CH_2C(CH_3)H$—, —$C(CH_3)HC(CH_3)H$—, —CH($R_g$)CH($R_g$)—, —O—$CH_2CH_2$—, —O—$C(CH_3)HCH_2$—, or —S—$CH_2CH_2$—.

A specific group of compounds are compounds wherein X and Y together are —$CH_2CH_2$—, —$CH_2CH_2CH_2$—, —CH=$CHCH_2$—, —O—$CH_2CH_2$—, —S—$CH_2CH_2$—, —S(O)—$CH_2CH_2$—, —$S(O)_2$—$CH_2CH_2$—, —$NR_f$—$CH_2CH_2$—, —$CH_2C(=O)$—, —$CH_2CH_2C(=O)$—, —$CH_2OC(=O)$—, or —$OCH_2C(=O)$—.

A specific group of compounds are compounds of formula (I) wherein X and Y together are —CH($R_g$)$CH_2$—, —CH($R_g$)CH($R_g$)$CH_2$—, or —O—$CH_2CH_2$—, wherein each $R_g$ is independently —$NR_qR_r$, —$S(O)_pR_s$, —$OR_r$, $C_{1-7}$alkyl, ($C_{1-7}$alkoxy)$C_{1-7}$alkyl, aryl, (aryl)$C_{1-7}$alkyl, heteroaryl, (heteroaryl)$C_{1-7}$alkyl, or (aryl)oxy$C_{1-7}$alkyl.

A specific group of compounds are compounds of formula (I) wherein X and Y together are —$C(=O)CH_2$—, —$CH_2C(=O)$—, —$C(=S)CH_2$—, —$CH_2C(=S)$—, —$C(=O)CH_2CH_2$—, —$CH_2C(=O)CH_2$—, —$CH_2CH_2C(=O)$—, —$C(=S)CH_2CH_2$—, —$CH_2C(=S)CH_2$—, or —$CH_2CH_2C(=S)$—.

A specific group of compounds are compounds wherein n is 1 and $R_1$ is $C_{1-7}$alkyl, $C_{1-7}$alkoxy, or halo.

A specific group of compounds are compounds wherein n is 1 and $R_1$ is methyl, methoxy, chloro, or fluoro.

A specific group of compounds are compounds wherein X and Y together are a 2, 3, or 4 membered saturated or partially unsaturated chain comprising one or more carbon atoms and optionally comprising one oxy (—O—), thio (—S—), sulfinyl (—SO—), sulfonyl ($S(O)_2$—), or $NR_f$ in the chain; wherein the chain is optionally substituted on each carbon with oxo (=O), hydroxy, or $C_{1-7}$alkoxy, or with one or two substituents independently selected from the group consisting of $C_{1-7}$alkyl, ($C_{1-7}$alkoxy)$C_{1-7}$alkyl, aryl, (aryl)$C_{1-7}$alkyl, heteroaryl, (heteroaryl)$C_{1-7}$alkyl, and (aryl)oxy$C_{1-7}$alkyl; or wherein the chain is optionally substituted on a carbon with a 4, 5, or 6 membered spirocyclic carbon ring; or wherein the chain is optionally substituted on two adjacent atoms with a 2, 3, or 4 membered alkylene chain (e.g. —$CH_2CH_2$—, —$CH_2CH_2CH_2$—, or —$CH_2CH_2CH_2CH_2$—) forming a ring that is fused to the ring comprising X and Y;

When X and Y together, or $R_1$, is a "partially unsaturated" group, such group may comprise one or more (e.g. 1 or 2) carbon-carbon double or triple bonds. For example, when $R_1$ is a partially unsaturated $C_{1-7}$alkyl, it can be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 2,4-hexadienyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 3-hexen-5-ynyl, 4-hexynyl, or 5-hexynyl.

Specifically, the invention also provides a method for treating or preventing anxiety, obesity, depression, schizophrenia, a stress related disease (e.g. general anxiety disorder), panic disorder, a phobia, obsessive compulsive disorder, post-traumatic-stress syndrome, immune system depression, a stress induced problem with the gastrointestinal or cardiovascular system, or sexual dysfunction in a mammal (e.g. a human) comprising administering a therapeutically effective amount of a compound of formula I, or a pharmaceutically acceptable salt thereof to the mammal.

Specifically, the invention also provides a method of treating or preventing anxiety, obesity, depression, or a stress related disease, comprising administering to a mammal (e.g. a human) in need of such treatment, a therapeutically effective amount of a compound of formula (I) or a pharmaceutically acceptable salt thereof.

Specifically, the invention also provides the use of a compound of formula (I) or a pharmaceutically acceptable salt thereof to prepare a medicament for treating or preventing anxiety, obesity, depression, schizophrenia, a stress related disease (e.g. general anxiety disorder), panic disorder, a phobia, obsessive compulsive disorder, post-traumatic-stress syndrome, immune system depression, a stress induced problem with the gastrointestinal or cardiovascular system, or sexual dysfunction in a mammal (e.g. a human).

Specifically, the invention also provides the use of a compound of formula (I) or a pharmaceutically acceptable salt thereof to prepare a medicament for treating or preventing anxiety, obesity, depression, or a stress related disease in a mammal (e.g. a human).

The invention also provides processes and intermediates useful for preparing compounds of formula (I). For example, an intermediate useful for preparing a compound of formula (I) wherein $R_2$ is hydrogen, is a corresponding compound of formula (I) wherein $R_2$ is a suitable protecting group. Thus the invention provides a compound of formula (I) wherein $R_2$ is a suitable protecting group, and wherein $R_1$, X, Y, and n have any of the values, specific values or prefered values defined herein. Suitable amine protecting groups, as well as methods for their preparation and removal are well known in the art, for example, see Greene, T. W.; Wutz, P. G. M. "Protecting Groups In Organic Synthesis" third edition, 1999, New York, John Wiley & sons, Inc. Prefered protecting groups include benzyloxycarbonyl (CBZ) and benzoyl.

The invention also provides intermediate compounds of formula 3, 9, 10, 11, 13, 15, and 17–20 as shown in FIGS. 1–6, wherein $R_2$ is a protecting group.

The invention also provides intermediate salts that are useful for preparing or purifying compounds of formula (I). Suitable methods for preparing salts are known in the art and are disclosed herein. For example, the preparation of an oxylate salt is shown in Example 41. As will be apparent to one skilled in the art, such salts can be converted to the corresponding free-base or to another salt using known methods.

For example, compounds of formula I wherein $R_2$ is $C_{1-4}$alkyl, $C_{1-4}$alkanoyl, arylcarbonyl, (aryl)$C_{1-2}$alkyl, $C_{1-4}$alkoxycarbonyl, aryloxycarbonyl, arylsulfonyl, or (aryl)methoxycarbonyl, wherein any aryl is optionaly substituted with 1, 2, or 3 substituents independently selected from $C_{1-4}$alkyl and trifluoromethyl, are particularly useful as intermediates for preparing corresponding compounds of formula I wherein $R_2$ is hydrogen. Preferred compounds of formula I that are useful for preparing compounds of formula I wherein $R_2$ is hydrogen are compounds wherein $R_2$ is methyl, ethyl, propyl, isopropyl, acetyl, tert-butoxycarbonyl, benzyloxycarbonyl, benzyl, or p-toluenesulfonyl.

The invention also provides a method for preparing a compound of formula (I) wherein $R_2$ is hydrogen comprising deprotecting a corresponding compound of formula (I) wherein $R_2$ is a suitable nitrogen protecting group.

Compounds of the invention can generally be prepared using the synthetic schemes illustrated in FIGS. 1–6. Starting materials can be prepared by procedures described in these schemes or by procedures that would be well known to one of ordinary skill in organic chemistry. The variables used in the Schemes are as defined below or as in the claims.

Compounds of formula I can be prepared by reactions outlined in FIG. 1. Step 1 involves formation of intermediate N-nitroso compounds by treatment with isoamylnitrite or other standard acid catalyzed N-nitrosation conditions. The resulting N-nitroso compounds are directly reduced to their corresponding hydrazines (2) by treatment with lithium aluminum hydride in a suitable solvent such as tetrahydrofuran. In step 2, hydrazines (2) are condensed by acid catalysis with 1-benzoylhexahydroazepine, which is available by the process described in *J. Org. Chem.*, Vol. 33, pp 3187–95 (1968), or with benzyl 4-oxo-1-azepanecarboxylate, the synthesis of which is described in the experimental section. Fischer/Indole cyclization of the crude hydrazines provides the desired azepinoindoles (3). The Fischer/Indole cyclization can be effected with a variety of acids such as formic acid, acetic acid, trifluoroacetic acid, aqueous hydrochloric acid, aqueous sulfuric acid, or polyphosphoric acid. Step 3 is effected by either catalytic hydrogenolysis when $R_2$ is benzyl or benzyloxycarbonyl, or by base catalyzed hydrolysis in a suitable solvent such as ethylene glycol when $R_2$ is benzoyl. Azepinoindoles 4 (wherein when $R_2$ is hydrogen) can conveniently be isolated as their hydrochloride salts.

It will be apparent to those skilled in the art that many of the requisite amines (1) are commercially available or known in the literature. The necessary 3,4-dihydro-1(2H)-quinolinylamines required for Examples 1–13 are known compounds. Indolines required for the synthesis of Examples 14–18 are either commercially available or readily prepared from known indoles following the procedure described in *Synthesis* pp. 859–60 (1977). For the benzmorpholines and benzthiomorpholines required for Examples 19–25, the synthetic route shown in FIG. 2 was followed. Nitrophenols 5 were alkylated with ethyl bromoacetate derivatives to afford 6. The nitro moiety is then reduced with Pd/C in the presence of hydrogen in a suitable solvent such as ethanol. In situ cyclization gives amide 7, which is then reduced with borane to provide the required amines 8.

Figure 3:
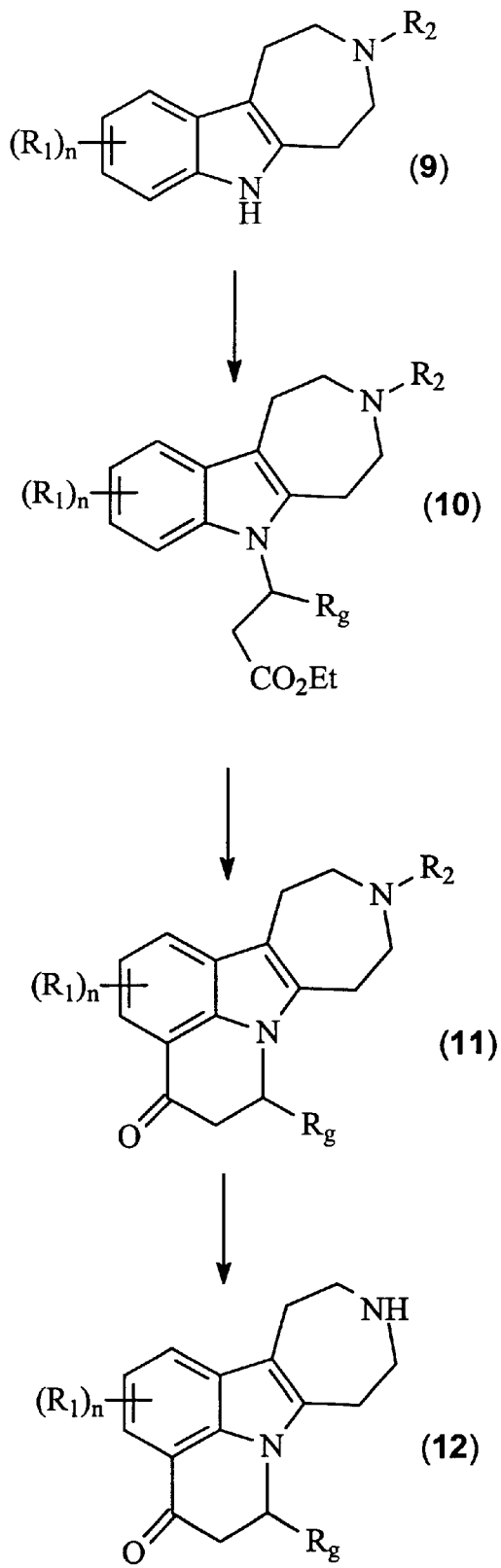

Compounds of formula I can also be prepared by the reactions outlined in FIG. 3. Azapinoindoles 9 are known in the literature (*J Med Chem.*, 1968, 11, 101–106) and can participate in a Michael conjugate addition into ethyl acrylate, or a derivative thereof, in the presence of a suitable base such as cesium carbonate. Base-catalyzed hydrolysis of esters 10 gives crude acids which then undergo intramolecular Friedel-Crafts acylation in an acidic media (e.g. polyphosphoric acid or Eaton's reagent). When $R_2$ is benzoyl, azepinoindoles 12 can be obtained from base-catalyzed hydrolysis in tetrahydrofuranlmethanol.

Figure 4:
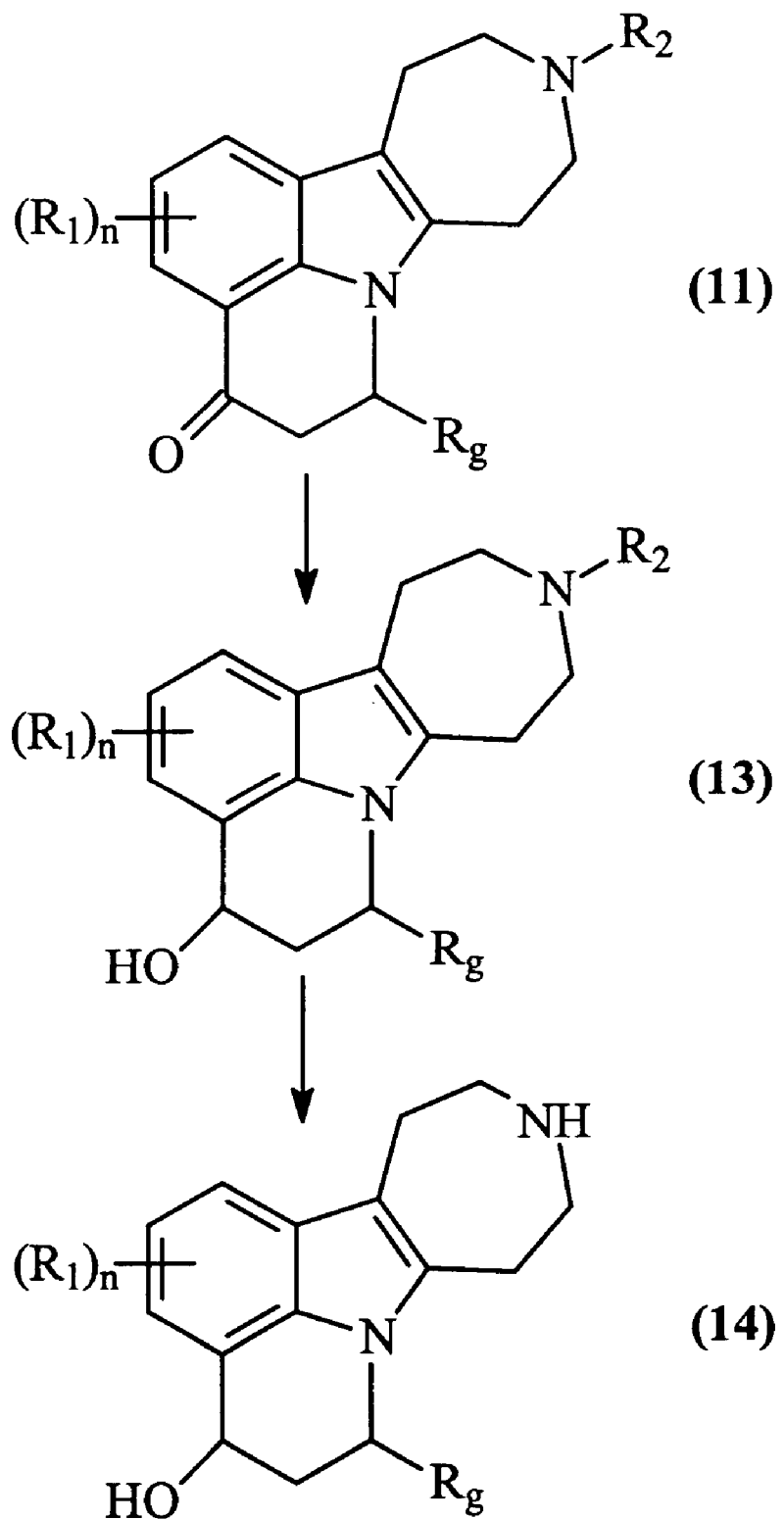
Figure 5:
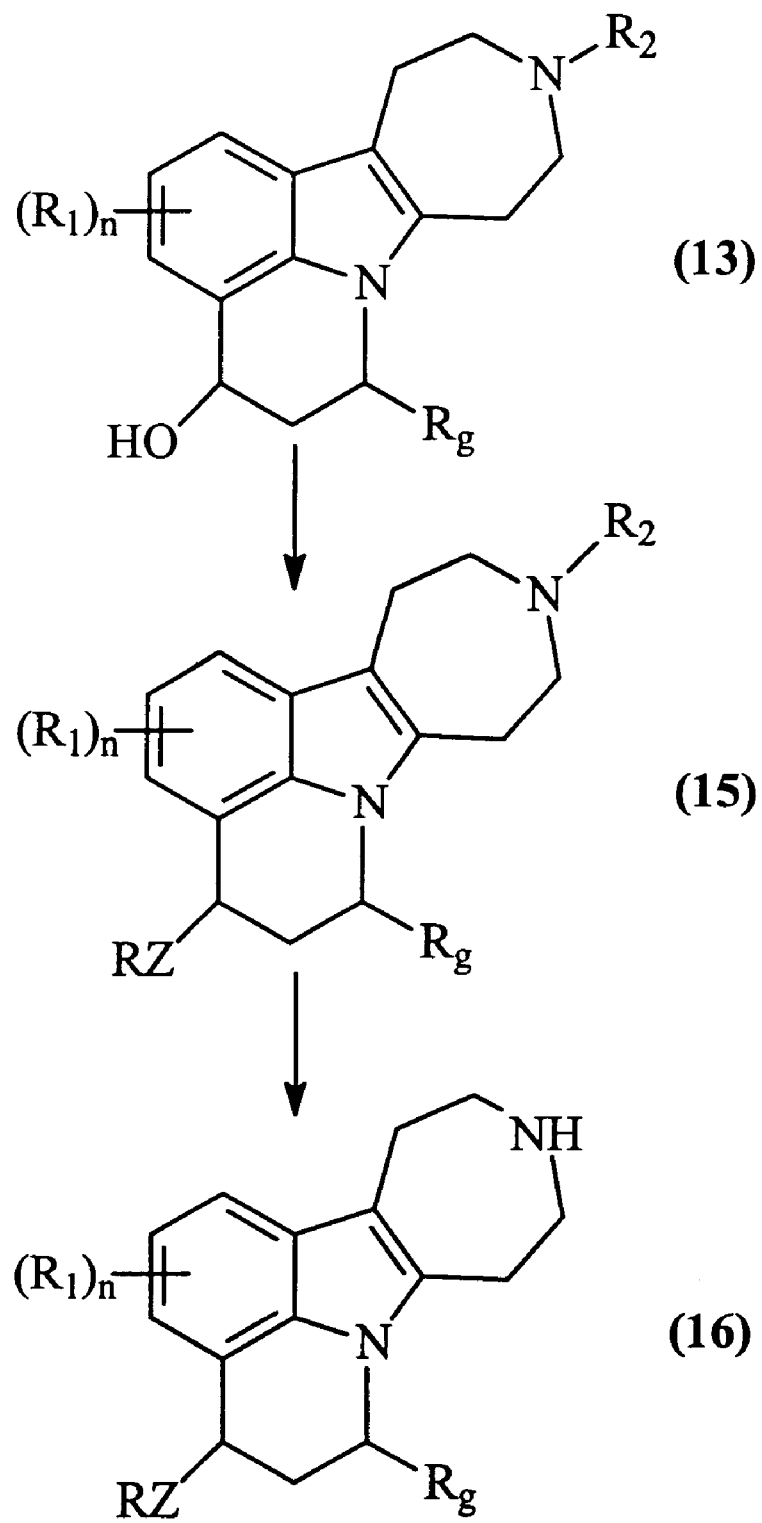

Aryl ketones 11 can be used as intermediates in the synthesis of additional compounds of formula I as shown in FIG. 4. The ketone moiety is reduced with sodium borohydride to give alcohols 13. When $R_2$ is benzoyl, base-catalyzed hydrolysis of alcohols 13 gives azepinoindoles 14. Alternatively, alcohols 13 can also be used as intermediates in the synthesis of additional compounds of formula I as shown in FIG. 5. Alcohols 13 can be alkylated with an alkyl halide in the presence of sodium hydride or with phenols via Mitsunobu reaction conditions. The use of thiols or amines in the Mitsunobu reaction can give additional derivatives. Removal of $R_2$ gives azepinoindoles 16.

Figure 6:
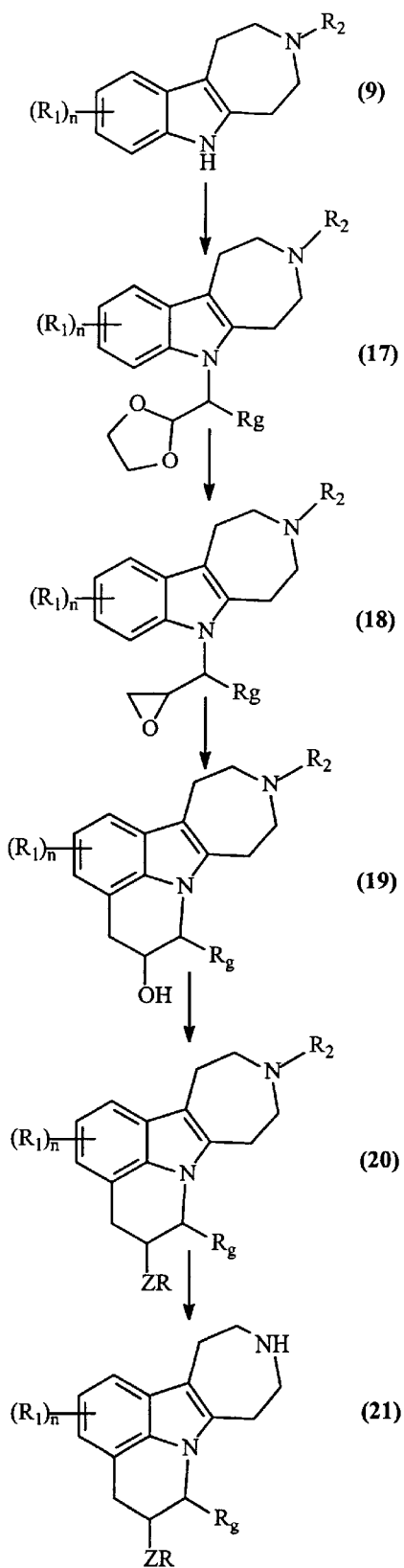

Azepinoindoles 9 can also be used to make compounds of formula I as shown in FIG. 6. Alkylation of 9 with 2-bromomethyl-1,3-dioxolane, or a derivative thereof, gives compounds 17. Acid-catalyzed removal of the acetal group leads to an aldehyde that can be reacted with trimethylsulfoxonium iodide and sodium hydride to give epoxides 18. Use of a Lewis acid, such as boron trifluoride diethyl etherate, would lead to alcohols 19. These alcohols could be treated as above to give azepinoindoles 20 and 21.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, (α-ketoglutarate, and (α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 mg/kg, preferably about 0.1 to about 50 mg/kg, and more preferably about 0.1 to about 10 mg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

The ability of a compound of the invention to act as a 5-HT receptor agonist or antagonist can also be determined using in vitro and in vivo assays that are known in the art. The invention provides compounds of formula I that act as either agonists or as antagonists of one or more 5-HT receptor subtypes. The compounds Exemplified herein are 5-HT ligands, which typically displace >50% of a radiolabeled test ligand from one or more 5-HT receptor subtype at a concentration of 1 □M. The procedures used for testing such displacement are well known and would be readily available to one skilled in the art.

Test A

Materials and Methods

Human 5-$HT_{2C}$ receptor was cloned from a thalamus cDNA library (see D. Julius, *Sciencie*, 698, 241, 558–564). The gene was inserted into expression vectors containing resistance genes as selectable markers. The resulting DNA constructs were transfected into HEK293 cells and were screened for expression by binding with [$^3$H]mesulergine (see A. Pazos, et al. *J. Pharmacol.*, 1984, 106, 539–546). The receptor was used under license from D. J. Julius at Columbia University.

Growth of the Cell Line and Membrane Preparation

The HEK293-h5-$HT_{2C}$-5 cell line was seeded from frozen stocks into DMEM high glucose salts medium supplemented with sodium pyruvate, Penicillin/Streptomycin solution, G418 (0.25 g/L), hygromycin B (48 mg/ml), and Fetal Bovine Serum (3%). The cells were first grown in T-75 flasks, passaged to T-225 flasks, and finally onto 24.5×24.5 cm NUNC culture dishes. At approximately 90% confluency, the cells were rinsed with ice-cold PBS and scraped from the NUNC plates using 3M squeegees. The cells were broken with a VirTishear homogenizer. The remaining particulate matter was removed by low-speed centrifugation. Finally, the membranes were concentrated by high-speed centrifugation and resuspended in binding buffer, 50 mM TRIS, 5 mM $MgCl_2$, pH 7.4. The preparation was held in a water-ice slurry while a pilot binding assay was performed (1.5 hours), and then quick-frozen in aliquots appropriate for 1 tube for each 96-well assay plate.

Scintillation Proximity Radioligand Binding Assay

Assays were performed in Wallac microtitre PET plates designed for the Wallac microBeta LSC. Binding reactions contained test compound (11 µl), [$^3$H]serotonin (124 Ci/mmol, 11 µl for final 4 nM) and bead-membrane mixture (178 µl). The test compound was replaced by water to determine total binding, or by mianserin (5 µM) to define non-specific binding.

The bead-membrane mixture was made by adding 100 mg Wheatgerm Agglutinin SPA beads (Amersham) and membrane preparation (2–5 mg protein) in a total of 8 ml binding buffer for each 96-well assay plate. The mixture was stirred gently for 30 minutes at room temperature, followed by centrifugation (1000 RPM, Beckman Accuspin FR) for 10 minutes. The supernatant, containing excess membrane, was aspirated, and the beads resuspended in 18.5 ml binding buffer for each assay plate. The washed bead-membrane mix was then poured into a reagent reservoir. The mixture was pipetted into the assay plate with a multi-channel pipetter, maintaining constant stirring during pipetting.

After the reactions were complete, the plates were sealed with plastic tape and placed on a gyrotory shaker (150 rpm) for 5 minutes. After shaking, room temperature incubation continued for 2 hours. Finally, the plates were loaded into counting cassettes and counted with the wallac microBeta LSC.

Bindind Constant (KI) Determinations

Eleven half-log serial dilutions of test compounds were made in water using the PE/Cetus Pro/Pette petter. These dilutions were distributed to assay plates using the same instrument, followed by radioligand and the bead-membrane mixture prepared as described above. The specifically bound cpm obtained were fit to a one-site binding model using GraphPad Prism ver. 2.0. Estimated $IC_{50}$ values were converted to Ki's using the Cheng-Prusoff equation (Cheng, Y. C. et al., *Biochem. Pharmacol.*, 22, 3099–108 (1973)), using a Kd value of 7 nM and an experimentally determined radioligand concentration.

Results

Data from Test A for representative compounds of formula I is shown in Table 1.

TABLE 1

| Example Number | Receptor binding $5HT_{2c}Ki$ (nM) |
|---|---|
| 1 | 13 |
| 2 | 80 |
| 3 | 27 |
| 4 | 83 |

TABLE 1-continued

| Example Number | Receptor binding $5HT_{2c}Ki$ (nM) |
|---|---|
| 5 | 33 |
| 6 | 44 |
| 7 | 77 |
| 8 | 51 |
| 9 | 26 |
| 10 | 70 |
| 11 | 96 |
| 12 | 41 |
| 13 | 45 |
| 14 | 28 |
| 15 | 24 |
| 16 | 361 |
| 17 | 65 |
| 18 | 52 |
| 19 | 144 |
| 20 | 3.8 |
| 21 | 16 |
| 22 | 2.3 |
| 23 | 13 |
| 24 | 29 |
| 25 | 8 |
| 26 | 29 |
| 27 | 5.1 |

DESCRIPTION OF PREFERRED EMBODIMENTS

PREPARATION 1.

Preparation of 1-benzyl 4-ethyl 5-oxo-1,4-azepanedicarboxylate

A dry 500 ml 3-neck flask was charged with benzyl 4-oxo-1-piperidinecarboxylate (35.08 g, 150 mmol). It was dissolved in 130 ml $Et_2O$ and cooled to −45° C. Ethyldiazoacetate (20.5 ml, 195 mmol) and boron trifluoride ethyl ether (19.4 ml, 158 mmol) were added simultaneously by syringe pump over 45 minutes. The temperature was kept below −25° C. The reaction was stirred for 30 minutes longer, and then quenched with sat. $NaHCO_3$. The ice bath was removed. The reaction was diluted with EtOAc (250 ml) and $H_2O$ (150 ml). The layers were separated, and the organic phase was dried over $MgSO_4$. It was concentrated under reduced pressure to an orange oil. The product was purified by flash chromatography (silica gel, 40% EtOAc/hexane), yielding product as pale yellow oil (42.1 g, 88%). $^1$H NMR ($CDCl_3$) δ 7.39–7.31, 5.15–5.12, 4.42–4.17, 3.96–3.83, 3.75–3.70, 3.65, 3.54–3.37, 2.08–2.03, 1.29–1.24; IR (liq.) 1743, 1702, 1476, 1455, 1443, 1425, 1371, 1318, 1295, 1238, 1213, 1178, 1098, 1068, 1028 $cm^{-1}$.

Preparation of benzyl 4-oxo-1-azepanecarboxylate

A solution of potassium hydroxide (24.6 g, 375 mmol) in $H_2O$ (400 ml) was added to a solution of 1-benzyl 4-ethyl 5-oxo-1,4-azepanedicarboxylate (40.0 g, 125 mmol) in ethanol (400 ml). The resulting mixture was heated at reflux for 2.5 hours. Reaction was then cooled to rt., the ethanol was removed under reduced pressure, and was diluted with 200 ml brine and 300 ml ethyl acetate. The layers were separated, and the aqueous phase was extracted with ethyl acetate (2×100 ml). The combined organic layers were washed with brine, dried over $MgSO_4$, and concentrated to an orange oil in vacuo. The product was isolated by flash chromatography (silica gel, 40% EtOAc/hexane) yielding a clear, colorless oil (22.6 g, 73%). $^1$H NMR ($CDCl_3$) δ

7.31–7.30, 5.12, 3.65–3.63, 2.68–2.60, 1.81–1.78; IR (liq.) 1698, 1475, 1454, 1442, 1423, 1331, 1320, 1295, 1270, 1241, 1191, 1165, 1091, 900, 699 cm$^{-1}$.

EXAMPLE 1

Preparation of 5,6,9,10,11,12-Hexahydro-4H,8H-azepino[4',5':4,5]pyrrolo[3,2,1-ij]quinoline Hydrochloride

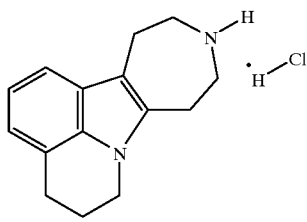

Step 1. Preparation of 3,4-Dihydro-1(2H)-quinolinylamine hydrochloride.

A neat reaction between 1,2,3,4-tetrahydroquinoline (3.71 g, 27.9 mmol) and isoamylnitrite (8.72 g, 74.4 inmol) was allowed to stir for 1 hour. The residual isoamylnitrite was removed under reduced pressure and the N-nitroso intermediate was taken up in tetrahydrofuran (20 ml). This solution was added dropwise to a refluxing solution of lithium aluminum hydride in tetrahydrofuran (55 ml, 1M, 55.0 mmol). One hour after the addition was complete, the reaction was cooled to 0° C. and quenched. The reaction was filtered, concentrated under reduced pressure, and extracted into ether. The ethereal solution was washed with water, brine and dried over anhydrous potassium carbonate. The resulting brown oil (4.11 g) was trapped as the hydrochloride salt and recrystallized from methanolethyl acetate\hexanes to provide the title compound (mp 186–189° C.). $^1$H NMR (CDCl$_3$) δ 10.55, 7.31, 7.10, 6.98, 6.87, 3.59, 2.74, 2.05; IR (drift) 3053, 2956, 2940, 2868, 2841, 2835, 2724, 2667, 1603, 1586, 1580, 1567, 1545, 1499, 747 cm$^{-1}$.

Step 2. Preparation of benzyl 5,6,8,9,11,12-hexahydro-4H,10H-azepino[4',5':4,5]pyrrolo[3,2,1-ij]quinoline-10-carboxylate.

A solution of 3,4-dihydro-1(2H)-quinolinylamine (2.97 g, 20.1 mmol), benzyl 4-oxo-1-azepanecarboxylate (4.96 g, 20.1 mmol), and glacial acetic acid (0.2 ml) in ethanol (200 ml) was allowed to reflux for 2.5 hours. The reaction was then cooled and evaporated in vacuo. The hydrazone product was purified by flash chromatography (90 g SiO$_2$, 1% MeOH/CH$_2$Cl$_2$) providing benzyl 4-[3,4-dihydro-1(2H)-quinolinylimino]-1-azepanecarboxylate (7.55 g) as an oil. To a solution of benzyl 4-[3,4-dihydro-1(2H)-quinolinylimino]-1-azepanecarboxylate (6.79 g, 17.99 mmol) in ethanol (200 ml) was added trifluoroacetic acid (6.22 g, 53.96 mmol). The reaction was heated and allowed to stir at reflux for 2.5 hours, at which time it was cooled to rt., evaporated, and extracted into dichloromethane. This extract was washed with water, brine, dried with anhydrous sodium sulfate, and evaporated under reduced pressure. Crystallization from ethyl acetate/hexanes provided 2.93 g of the title compound (mp 131–133° C.). $^1$H NMR (CDCl$_3$) δ 7.38, 7.29, 7.00, 6.86, 5.19, 3.98, 3.78, 2.97, 2.24; IR (drift) 2947, 1699, 1473, 1420, 1358, 1260, 1250, 1235, 1216, 1101, 997, 764, 757, 746, 703 cm$^{-1}$.

Step 3. Preparation of 5,6,9,10,11,12-hexahydro-4H,8H-azepino[4',5':4,5]pyrrolo[3,2,1-ij]quinoline hydrochloride.

A mixture of benzyl 5,6,8,9,11,12-hexahydro-4H,10H-azepino[4',5':4,5]pyrrolo[3,2,1-ij]quinoline-10-carboxylate (2.42 g, 6.71 mmol) and 10% Pd/C (0.15 g) in ethanol (110 ml) was hydrogenated under 40 psi for 1.5 hours. The mixture was filtered through celite, rinsed with methanol, dichloromethane and evaporated. Methanolic hydrochloric acid is added and evaporated. The resulting product is recrystallized from methanol/ethyl acetate to give 1.40 g (80%) of the title compound (mp 261–263° C.). $^1$H NMR (CD$_3$OD) δ 7.25, 6.95, 6.84, 4.08, 3.48, 3.32, 3.28, 3.20, 2.95, 2.22; IR (drift) 2939, 2894, 2880, 2863, 2832, 2806, 2759, 2743, 2687, 2669, 2645, 2445, 1332, 1253, 743 cm$^{-1}$.

EXAMPLE 2

Preparation of 2-methyl-5,6,9,10,11,12-hexahydro-4H,8H-azepino[4',5':4,5]pyrrolo[3,2,1-ij]quinoline hydrochloride

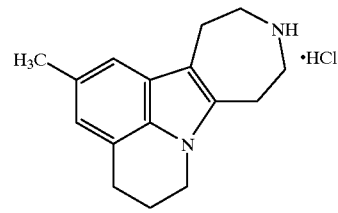

Following the general procedure of Example 1, making non-critical variations but starting with 6-methyl-1,2,3,4-tetrahydroquinoline, the title compound was obtained (mp 268–270° C.). $^1$H NMR (DMSO-d$_6$) δ 9.6, 6.99, 6.61, 3.98, 3.30, 3.16, 3.03, 2.81, 2.32, 2.08; IR (drift) 2965, 2949, 2934, 2902, 2880, 2850, 2823, 2791, 2769, 2695, 2659, 2438, 1458, 1251, 839 cm$^{-1}$.

EXAMPLE 3

Preparation of 1-methoxy-5,6,9,10,11,12-hexahydro-4H,8H-azepino[4',5':4,5]pyrrolo[3,2,1-ij]quinoline hydrochloride

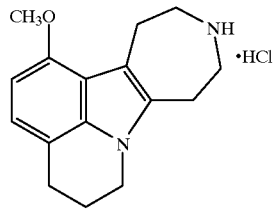

Following the general procedure of Example 1, making non-critical variations but starting with 7-methoxy-1,2,3,4-tetrahydroquinoline, the title compound was obtained (mp 277–279° C.). $^1$H NMR (DMSO-d6) δ 9.27, 6.65, 6.32, 3.96, 3.77, 3.29, 3.15, 2.78, 2.05; IR (drift) 2968, 2953, 2935, 2889, 2832, 2803, 2780, 2765, 2744, 2713, 1594, 1509, 1247, 1152, 781 cm$^{-1}$.

EXAMPLE 4

Preparation of 2-fluoro-5,6,9,10,11,12-hexahydro-4H,8H-azepino[4',5':4,5]pyrrolo[3,2,1-ij]quinoline hydrochloride

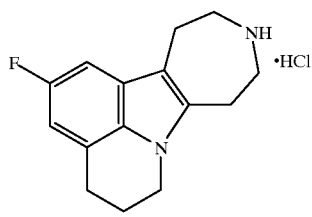

Following the general procedure of Example 1, making non-critical variations but starting with 6-fluoro-1,2,3,4-tetrahydroquinoline, the title compound was obtained (mp 273–276° C.). $^1$H NMR (CD$_3$OD) δ 6.94, 6.64, 4.07, 3.50, 3.44, 3.32, 3.28, 3.15, 2.94, 2.22; IR (drift) 2957, 2926, 2894, 2843, 2814, 2799, 2742, 2708, 2665, 2561, 2545, 2440, 1496, 1419, 1129 cm$^{-1}$.

EXAMPLE 5

Preparation of 6-methyl-5,6,9,10,11,12-hexahydro-4H,8H-azepino[4',5':4,5]pyrrolo[3,2,1-ij]quinoline hydrochloride

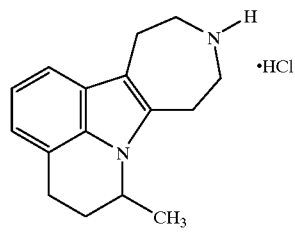

Following the general procedure of Example 1, making non-critical variations but starting with 2-methyl-1,2,3,4-tetrahydroquinoline, the title compound is obtained (mp 214–217° C.). $^1$H NMR (CDCl$_3$) δ 9.61, 7.25, 6.93, 6.84, 4.62, 3.32, 3.11, 2.87, 2.12, 2.01, 1.20; IR (drift) 2968, 2933, 2893, 2814, 2742, 2711, 2669, 2560, 2437, 1463, 1415, 1377, 1335, 1324, 742 cm$^{-1}$.

EXAMPLE 6

Preparation of 5-methyl-5,6,9,10,11,12-hexahydro-4H,8H-azepino[4',5':4,5]pyrrolo[3,2,1-ij]quinoline hydrochloride

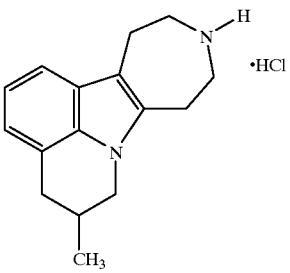

Following the general procedure of Example 1, making non-critical variations but starting with 3-methyl-1,2,3,4-tetrahydroquinoline, the title compound was obtained (mp 273–274° C.). $^1$H NMR (CDCl$_3$) δ 10.10, 7.27, 7.02, 6.88, 4.07, 3.51, 3.37, 3.31, 3.00, 2.65, 2.37, 1.20; IR (drift) 2956, 2923, 2899, 2867, 2831, 2800, 2766, 2686, 2670, 2562, 2448, 1454, 1428, 1257, 740 cm$^{-1}$.

EXAMPLE 7

Preparation of 4-Methyl-5,6,9,10,11,12-hexahydro-4H,8H-azepino[4',5':4,5]pyrrolo[3,2,1-ij]quinoline Hydrochloride

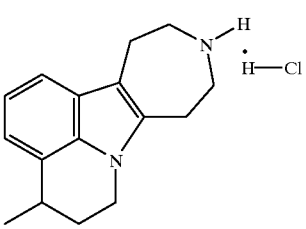

Following the general procedure of Example 1, making non-critical variations but starting with 4-methyl-1,2,3,4-tetrahydroquinoline, the title compound was obtained (mp 260–263° C.). $^1$H NMR (DMSO-d$_6$) δ 9.79, 7.22, 6.92, 6.85, 4.10, 4.00, 3.28, 3.20, 3.08, 2.15, 1.80, 1.30; IR (drift) 2959, 2939, 2891, 2873, 2860, 2811, 2800, 2739, 2709, 2662, 2647, 2553, 2542, 2437, 734 cm$^{-1}$.

EXAMPLE 8

Preparation of (+)-6-methyl-5,6,9,10,11,12-hexahydro-4H,8H-azepino[4',5':4,5]pyrrolo[3,2,1-ij]quinoline hydrochloride

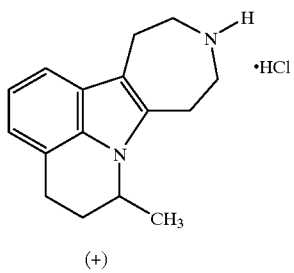

(+)

Following the general procedure of Example 5 making non-critical variations, preparative chiral HPLC was performed after step two on an EM ST 140R closed loop recycling prep HPLC system (EM Separations Technology). The column used was a 5×50 cm Chiralpak AD column at 30° C. The mobile phase was 5% isopropanol/95% heptane at a flow rate of 75 ml/min. Peak collection was monitored by UV detection at 285 nm. Following step three, the title compound was obtained (mp 196–199° C.).

EXAMPLE 9

Preparation of (−)-6-Methyl-5,6,9,10,11,12-hexahydro-4H,8H-azepino[4',5':4,5]pyrrolo[3,2,1-ij]quinoline Hydrochloride

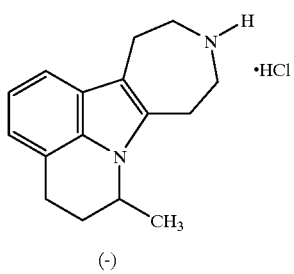

(−)

Following the general procedure of Example 5 making non-critical variations, preparative chiral HPLC was performed after step two on an EM ST 140R closed loop recycling prep HPLC system (EM Separations Technology). The column used was a 5×50 cm Chiralpak AD column at 30° C. The mobile phase was 5% isopropanol/95% heptane at a flow rate of 75 ml/min. Peak collection was monitored by UV detection at 285 nm. Following step three, the title compound was obtained (mp 196–199° C.); $[\alpha]^{25}_D = -27$ (c 0.88, DMSO).

EXAMPLE 10

Preparation of (+)-5-Methyl-5,6,9,10,11,12-hexahydro-4H,8H-azepino[4',5':4,5]pyrrolo[3,2,1-ij]quinoline hydrochloride

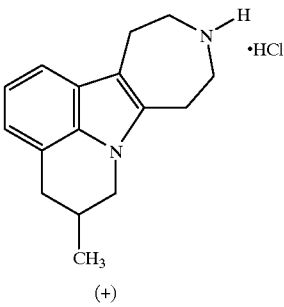

(+)

Following the general procedure of Example 6 making non-critical variations, preparative chiral HPLC was performed after step two on an EM ST 140R closed loop recycling prep HPLC system (EM Separations Technology). The column used was a 5×50 cm Chiralpak AD column at 30° C. The mobile phase was 5% isopropanol/95% heptane at a flow rate of 75 ml/min. Peak collection was monitored by UV detection at 285 nm. Following step three, the title compound was obtained (mp 259–262° C.); $[\alpha]^{25}_D = +20$ (c 0.28, DMSO).

EXAMPLE 11

Preparation of (−)-5-methyl-5,6,9,10,11,12-hexahydro-4H,8H-azepino[4',5':4,5]pyrrolo[3,2,1-ij]quinoline Hydrochloride

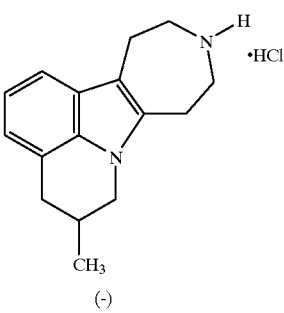

(−)

Following the general procedure of Example 6 making non-critical variations, preparative chiral HPLC was performed after step two on an EM ST 140R closed loop recycling prep HPLC system (EM Separations Technology). The column used was a 5×50 cm Chiralpak AD column at 30° C. The mobile phase is 5% isopropanol/95% heptane at a flow rate of 75 ml/min. Peak collection was monitored by UV detection at 285 nm. Following step three, the title compound was obtained (mp 259–262° C.); $[\alpha]^{25}_D = -21$ (c 0.43, DMSO).

EXAMPLE 12

Preparation of (+)4-Methyl-5,6,9,10,11,12-hexahydro-4H,8H-azepino[4',5':4,5]pyrrolo[3,2,1-ij]quinoline Hydrochloride

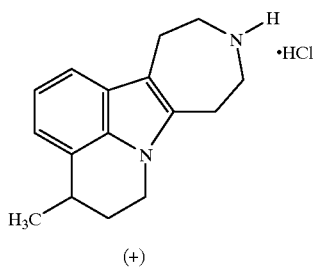

(+)

Following the general procedure of Example 7 making non-critical variations, preparative chiral HPLC was performed after step two on an EM ST 140R closed loop recycling prep HPLC system (EM Separations Technology). The column used was a 5×50 cm Chiralpak AD column at 30° C. The mobile phase was 5% isopropanol/95% heptane at a flow rate of 75 mnl/min. Peak collection was monitored by UV detection at 285 nm. Following step three, the title compound was obtained (mp 261–263° C.); $[\alpha]^{25}_D$=+39 (c 0.41, chloroform).

EXAMPLE 13

Preparation of (−)-4-Methyl-5,6,9,10,11,12-hexahydro-4H,8H-azepino[4',5':4,5]pyrrolo[3,2,1-ij]quinoline Hydrochloride

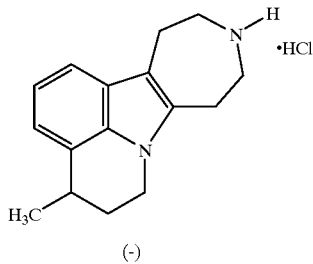

(−)

Following the general procedure of Example 7 making non-critical variations, preparative chiral HPLC was performed after step two on an EM ST 140R closed loop recycling prep HPLC system (EM Separations Technology). The column used was a 5×50 cm Chiralpak AD column at 30° C. The mobile phase was 5% isopropanol/95% heptane at a flow rate of 75 ml/min. Peak collection was monitored by TV detection at 285 nm. Following step three, the title compound is obtained (mp 261–263° C.); $[\alpha]^{25}_D$=−39 (c 0.51, chloroform).

EXAMPLE 14

Preparation of 4,5,8,9,10,1-Hexahydro-7H-azepino[4,5-b]pyrrolo[3,2,1-hi]indole Hydrochloride

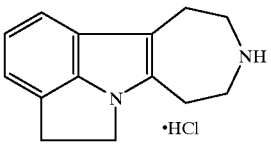

Following the general procedure outlined in EXAMPLE 1, starting with indoline, and utilizing 1-benzoylhexahydoazepine as the ketone in step 4, 5,7,8,10,11-hexahydro-9H-azepino[4,5-b]pyrrolo[3,2,1-hi]indol-9-yl(phenyl)methanone was obtained (mp 130–133° C.). $^1$H NMR (CDCl$_3$) δ 7.42, 7.08, 6.94, 6.85, 4.28, 4.00, 3.76, 3.63, 3.15, 2.88; MS (ESI+) for $C_{21}H_{20}N_2OH$ m/z 240.1 (M+H)$^+$.

Step 4 A mixture of 4,5,7,8,10,11-hexahydro-9H-azepino[4,5-b]pyrrolo[3,2,1-hi]indol-9-yl(phenyl)methanone (1.0 g, 3.2 mmol) and potassium hydroxide (0.89 g, 15.8 mmol) in ethylene glycol (10 ml) was heated under N$_2$ at 170° C. for 3 h. The reaction was cooled to rt, poured into water (50 ml) and extracted with methylene chloride (4×50 ml). The combine organics were washed with brine, dried over anhydrous potassium carbonate, and concentrated in vacuo. The residue was trapped as its HCl salt by treatment of a solution of the product in methanol with ethereal HCl. The resulting precipitate is recrystallized from methanol and ethyl acetate to give the desired product (0.4 g) (mp 249–250° C.). $^1$H NMR (CDCl$_3$) δ 7.16, 6.93, 6.82, 4.38, 3.74, 3.08, 2.94; IR (drift) 2925, 2916, 2885, 2847, 2805, 1510, 1462, 1409, 1350, 1336, 1306, 1279, 767, 758, 746 cm$^{-1}$.

EXAMPLE 15

Preparation of 2-Fluoro-4,5,8,9,10,11-hexahydro-7H-azepino[4,5-b]pyrrolo[3,2,1-hi]indole Hydrochloride

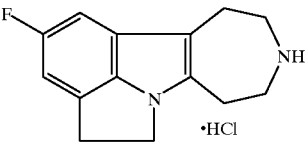

Following the general procedure outlined in EXAMPLE 14, and making non-critical variations but starting with 5-fluoro indoline, the title compound was obtained (mp 250–252° C.). $^1$H NMR (CD$_3$OD) δ 6.68, 6.43, 4.15, 3.47, 2.88, 2.76; IR (drift) 2930, 2911, 1661, 1507, 1412, 1354, 1261, 1171, 1112, 938, 857, 848, 839, 708, 688 cm$^{-1}$.

EXAMPLE 16

Preparation of 2-Methoxy-4,5,8,9,10,11-hexahydro-7H-azepino[4,5-b]pyrrolo[3,2,1-hi]indole Hydrochloride

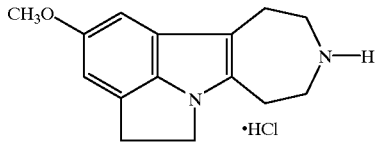

Following the general procedure outlined in EXAMPLE 14, and making non-critical variations but starting with 5-methoxy indoline, the title compound was obtained (mp 269–271° C.). $^1$H NMR (CD$_3$OD) δ 6.70, 6.57, 4.44, 3.80, 3.72, 3.45, 3.23, 3.16; IR (drift) 2974, 2948, 2908, 2891, 2841, 2817, 2805, 2769, 2718, 1509, 1421, 1255, 1244, 1233, 1142 cm$^{-1}$.

EXAMPLE 17

Preparation of 5-Methyl-4,5,8,9,10,11-hexahydro-7H-azepino[4,5-b]pyrrolo[3,2,1-hi]indole Hydrochloride

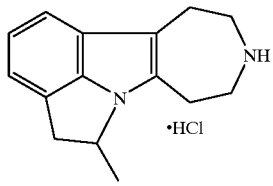

Following the general procedure outlined in EXAMPLE 1, and making non-critical variations but starting with 2-methyl indoline, the title compound was obtained (mp 243–246° C.). $^1$H NMR (CDCl$_3$) δ 7.13, 6.91, 7.80, 4.99–4.87, 3.93, 3.51–3.23, 3.17, 1.47; IR (drift) 2973, 2960, 2941, 2927, 2901, 2883, 2848, 2826, 2794, 2737, 2650, 2549, 2438, 1292, 751 cm$^{-1}$.

EXAMPLE 18

Preparation of 4,5-Dimethyl-4,5,8,9,10,11-hexahydro-7H-azepino[4,5-b]pyrrolo[3,2,1-hi]indole Hydrochloride

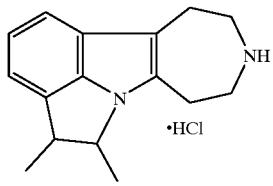

Following the general procedure outlined in EXAMPLE 1, and making non-critical variations but starting with 2,3-dimethyl indole, the title compound was obtained (mp 195–197° C.). $^1$H NMR (CD$_3$OD) δ 7.16, 6.92, 6.81, 4.40, 3.64, 3.53–3.35, 3.16, 1.54, 1.43; IR (drift) 2960, 2938, 2925, 2866, 2847, 2821, 2727, 2657, 2635, 2533, 2427, 1465, 1372, 1287, 746 cm$^{-1}$.

EXAMPLE 19

Preparation of 2,3,4,5,8b,9,10,11,12,12a-decahydro-1H-azepino[4',5':4,5]pyrrolo[3,2,1-jk]carbazole hydrochloride

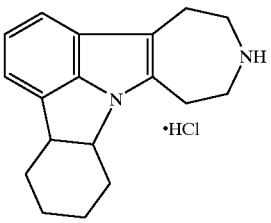

Following the general procedure outlined in EXAMPLE 1, and making non-critical variations but starting with 1,2,3,4 tetramethyl carbazole, the title compound was obtained (mp 210–212° C.). $^1$H NMR (CD$_3$OD) δ 7.16, 6.94, 6.82, 4.75, 4.14, 3.42, 3.25, 3.16, 2.12–1.96, 1.54, 1.41, 1.26, 1.08; IR (drift) 3046, 2936, 2929, 2846, 2810, 2744, 2633, 2541, 2519, 2429, 1460, 1328, 1290, 754, 744 cm$^{-1}$;

EXAMPLE 20

Preparation of 6-Methyl-1,2,8,9,10,11-hexahydro-7H-azepino[4,5-b][1,4]oxazino[2,3,4-hi]indole Hydrochloride

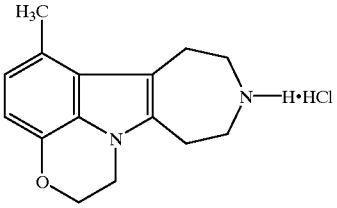

Step 5. Preparation of 6-Methyl-2H-1,4-benzoxazin-3(4H)-one.

To a solution of 4-methyl-2-nitrophenol (9.95 g, 65.0 mmol) in acetone (170 ml) was added, in one portion, potassium carbonate (10.8 g, 78.0 mnmol) and ethyl bromoacetate (7.9 ml, 71.5 mmol). The resulting mixture was heated at reflux for 3.5 hours. The acetone was removed in vacuo, and the resulting material was partitioned between ethyl acetate and water. The layers were separated, and the aqueous phase was extracted twice with ethyl acetate. The ethyl acetate layer was washed with saturated sodium bicarbonate, brine, dried over magnesium sulfate, filtered, and evaporated to afford an orange oil. The intermediate nitro compound was taken up in ethanol (150 ml) and hydrogenated with Pd/C (0.33 g) at 51 psi for 90 minutes. The mixture was filtered through celite, and the filtrate evaporated. The product was recrystallized from methanol to yield 7.29 g of the title compound as an off-white solid (mp 204–205° C.). $^1$H NMR (DMSO-d$_6$) δ 6.81–6.78, 6.70–6.67, 4.48, 2.18; MS [MH$^-$] 162.1.

Step 6. Preparation of 6-Methyl-3,4-dihydro-2H-1,4-benzoxazine.

To a solution of 6-methyl-2H-1,4-benzoxazin-3(4H)-one (7.02 g, 43.0 mmol) in tetrahydrofuran (130 ml) was added borane dimethylsulfide complex (43 ml, 10M). This solution was stirred at rt for 2.5 hours, then quenched with 1 M hydrochloric acid. The solvent was evaporated, and the residue was partitioned between saturated sodium bicarbonate and dichloromethane. The layers were separated, and the aqueous phase was extracted twice with dichloromethane. The dichloromethane layer was washed with brine, dried over magnesium sulfate, and evaporated to yield 5.1 g of the title compound as a pale yellow oil. $^1$H NMR (CDCl$_3$) δ 6.70–6.68, 6.49–6.46, 6.42, 4.24–4.21, 3.41–3.38, 2.22; MS [MH$^+$] 150.2.

Following the remainder of the general procedure of Example 1 (steps 1–3) and making non-critical variations but starting with 6-methyl-3,4-dihydro-2H-1,4-benzoxazine, the title compound was obtained (mp 271–273° C.). $^1$H NMR (CD$_3$OD) δ 6.59, 6.40, 4.44, 4.17, 3.52, 3.49, 3.27, 3.24, 2.57; IR (drift) 2979, 2957, 2934, 2872, 2855, 2828, 2792, 2760, 2746, 2683, 2652, 1511, 1265, 1243, 1223 cm$^{-1}$.

EXAMPLE 21

Preparation of 1,2,8,9,10,11-Hexahydro-7H-azepino[4,5-b][1,4]oxazino[2,3,4-hi]indole Hydrochloride

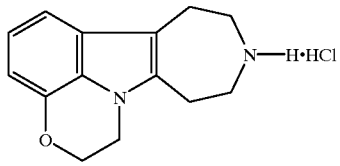

Following the general procedure of Example 20 but starting with 2 H-1,4-Benzoxazine-3(4H)-one, utilizing 1-benzoylhexahydoazepine as the ketone in the hydrazone formation of step two, and thus the deprotection sequence described in step 4 of example 14, the title compound was obtained (mp 217–219° C.). $^1$H NMR (DMSO-d$_6$) δ 9.6, 7.01, 6.85, 6.50, 4.46, 4.18, 3.28–3.08, 2.50; IR (drift) 2949, 2925, 2878, 2843, 2812, 2758, 2689, 2673, 1499, 1328, 1247, 1036, 872, 771, 729 cm$^{-1}$.

EXAMPLE 22

Preparation of 6-Chloro-1,2,8,9,10,11-hexahydro-7H-azepino[4,5-b][1,4]oxazino[2,3,4-hi]indole Hydrochloride

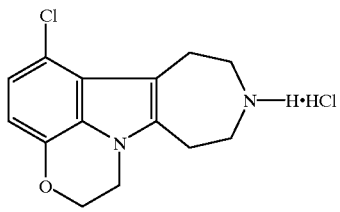

Following the general procedure of Example 20 and making non-critical variations but starting with 2-amino-4-chlorophenol, the title compound was obtained (mp decompose >275° C.). $^1$H NMR (CD$_3$OD) δ 6.84, 6.50, 4.49–4.48, 4.22–4.20, 3.65–3.63, 3.53–3.48, 3.30–3.27; IR (free amine) (drift) 2932, 2897, 2882, 2823, 1495, 1466, 1379, 1355, 1323, 1277, 1269, 1236, 1217, 1199, 1014 cm$^{-1}$.

EXAMPLE 23

Preparation of 5-Fluoro-1,2,8,9,10,11-hexahydro-7H-azepino[4,5-b][1,4]oxazino[2,3,4-hi]indole Hydrochloride

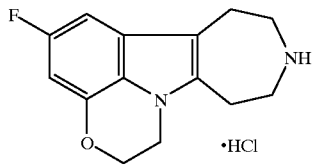

Following the general procedure of Example 20 and making non-critical variations but starting with 5-fluoro-2-nitrophenol, the title compound was obtained (mp decompose >250° C.). $^1$H NMR (CD$_3$OD) δ 6.76–6.72, 6.38–6.33, 4.52–4.49, 4.20–4.17, 3.51–3.43, 3.28–3.25, 3.18–3.14; IR (drift) 2950, 2855, 2805, 2767, 2757, 2710, 2675, 2651, 2565, 2449, 1645, 1591, 1500, 1333, 1109 cm$^{-1}$.

EXAMPLE 24

Preparation of 5-Methyl-1,2,8,9,10,11-hexahydro-7H-azepino[4,5-b][1,4]oxazino[2,3,4-hi]indole Hydrochloride

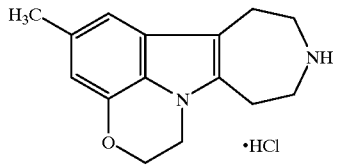

Following the general procedure of Example 20 but starting from 5-methyl-2-nitrophenol and using glacial acetic acid for the cyclization in step 3, the title compound was obtained (mp 274–275° C.). $^1$H NMR (CD$_3$OD) δ 6.81, 6.37, 4.44, 4.12, 3.48–3.41, 3.22, 3.15, 2.36; IR (drift) 2983, 2965, 2940, 2880, 2856, 2822, 2809, 2758, 2731, 2667, 1590, 1503, 1331, 1031, 847 cm$^1$.

EXAMPLE 25

Preparation of 6-Fluoro-1,2,8,9,10,11-hexahydro-7H-azepino[4,5-b][1,4]oxazino[2,3,4-hi]indole Hydrochloride

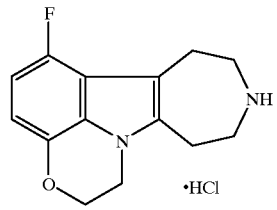

Following the general procedure of Example 20 but starting from 4-fluoro-2-nitrophenol and using p-toluene sulfonic acid for the cyclization in step 3, the title compound was obtained (mp 257–259° C.). $^1$H NMR (CD$_3$OD) δ 6.55–6.49, 6.43–6.40, 4.44, 4.17, 3.49–3.44, 3.38–3.33, 3.26–3.23; IR (drift) 2949, 2876, 2845, 2815, 2768, 2685, 2676, 2626, 1511, 1362, 1277, 1224, 1023, 881, 791 cm$^{-1}$.

EXAMPLE 26

Preparation of 2-Methyl-1,2,8,9,10,11-hexahydro-7H-azepino[4,5-b][1,4]oxazino[2,3,4-hi]indole Hydrochloride

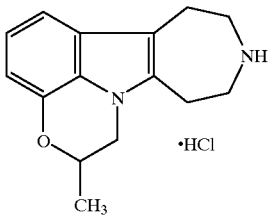

Following the general procedure of Example 20 and making non-critical variations but starting with 2-nitrophenol and ethyl-2-bromopropionate, the title compound was obtained (mp 255–257° C.). $^1$H NMR (CD$_3$OD) δ 7.01, 6.88, 6.54, 4.40–4.35, 4.30, 3.68–3.63, 3.49–3.42, 3.25–3.17, 1.51; IR (drift) 2967, 2931, 2809, 2790, 2736, 2711, 2655, 2647, 2557, 2439, 1502, 1377, 1322, 1243, 794 cm$^{-1}$.

EXAMPLE 27

Preparation of 1,2,8,9,10,11-Hexahydro-7H-azepino[4,5-b][1,4]thiazino[2,3,4-hi]indole Hydrochloride

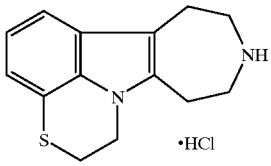

Following the general procedure of Example 21 but starting from 2H-1,4-benzothiazin-3(4H)-one and using 10% sulfuric acid for the cyclization in step 3, the title compound was obtained (mp 263° C.). $^1$H NMR (CD$_3$OD) δ 7.24, 6.94, 6.87, 3.36–3.24, 3.12–3.10; IR (drift) 2937, 2929, 2862, 2814, 2718, 2663, 2626, 2594, 2544, 2428, 1463, 1412, 1335, 782, 739 cm$^{-1}$.

EXAMPLE 28

Preparation of 2,2-Dimethyl-1,2,8,9,10,11-hexahydro-7H-azepino[4,5-b][1,4]oxazino[2,3,4-hi]indole Hydrochloride

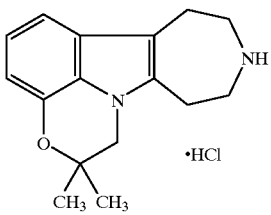

Following the general procedure of Example 20 but starting with 2-nitrophenol and ethyl-2-bromoisobutyrate, and using p-toluene sulfonic acid for the cyclization in step 3, the title compound was obtained (mp decompose >260° C.). $^1$H NMR (CD$_3$OD) δ 7.03, 6.92, 6.52, 3.96, 3.53–3.46, 3.26–3.20, 1.41; IR (drift) 2972, 2948, 2858, 2824, 2766, 2751, 1583, 1498, 1385, 1332, 1245, 1202 cm$^{-1}$.

EXAMPLE 29

Preparation of 4-Fluoro-1,2,8,9,10,11-hexahydro-7H-azepino[4,5-b][1,4]oxazino[2,3,4-hi]indole Maleic Acid

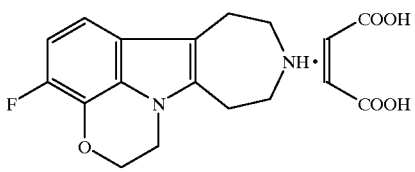

Following the general procedure of Example 20 but starting with 2-fluoro-6-nitrophenol, using p-toluene sulfonic acid for the cyclization in step 3, and preparing the Maleic acid salt, the title compound was obtained (mp 176–177° C.). $^1$H NMR (CD$_3$OD) δ 6.95, 6.78, 6.24, 4.51, 4.19, 3.42–3.50, 3.23, 3.16; IR (drift) 3009, 2925, 2899, 2879, 2835, 2786, 2714, 1705, 1626, 1550, 1531, 1526, 1486, 1358 cm$^{-1}$.

EXAMPLE 30

Preparation of 4-Chloro-1,2,8,9,10,11-hexahydro-7H-azepino[4,5-b][1,4]oxazino[2,3,4-hi]indole Maleic Acid

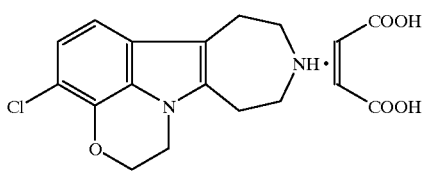

Following the general procedure of Example 20 but starting with 6-chloro-2-nitrophenol, using p-toluene sulfonic acid for the cyclization in step 3, and preparing the Maleic acid salt, the title compound was obtained (mp 183–184° C.). $^1$H NMR (CD$_3$OD) δ 6.99, 6.91, 6.24, 4.56, 4.20, 3.43–3.51, 3.23, 3.16; IR (drift) 1645, 1639, 1627, 1608, 1568, 1536, 1517, 1497, 1476, 1385, 1377, 1372, 1355, 1196 cm$^{-1}$.

EXAMPLE 31

Preparation of 5-Chloro-1,2,8,9,10,11-hexahydro-7H-azepino[4,5-b][1,4]oxazino[2,3,4-hi]indole Maleic Acid

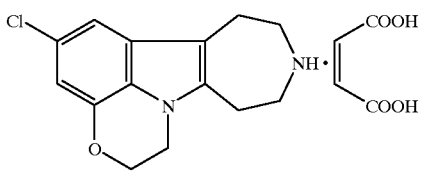

Following the general procedure of Example 20 but starting with 5-chloro-2-nitrophenol, using TFA in EtOH for the cyclization in step 3, and preparing the Maleic acid salt, the title compound was obtained (mp 177–179° C. ). ¹H NMR (CD₃OD) δ 7.05, 6.55, 6.24, 4.50, 4.18, 3.42–3.50, 3.23–3.25, 3.14–3.16; IR (drift) 2892, 2867, 2779, 2745, 1627, 1569, 1536, 1491, 1466, 1451, 1369, 1329, 1024 cm⁻¹.

EXAMPLE 32

Preparation of 6-(trifluoromethyl)-1,2,8,9,10,11-Hexahydro-7H-azepino[4,5-b][1,4]oxazino[2,3,4-hi]indole Hydrochloride

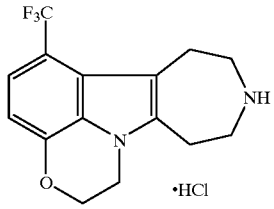

Following the general procedure of Example 20 but starting with 2-nitro-4-(trifluoro methyl)-phenol, using p-toluene sulfonic acid for the cyclization in step 3, the title compound was obtained (mp 248–250° C. ). ¹H NMR (CD₃OD) δ 7.30, 6.61, 4.55, 4.26, 3.46–3.53; IR (drift) 2815, 2797, 2741, 2670, 2560, 1583, 1333, 1244, 1198, 1158, 1107, 1094, 1060, 1021 cm⁻¹.

EXAMPLE 33

Preparation of 5,6-Difluoro-1,2,8,9,10,11-hexahydro-7H-azepino[4,5-b][1,4]oxazino[2,3,4-hi]indole Maleic Acid

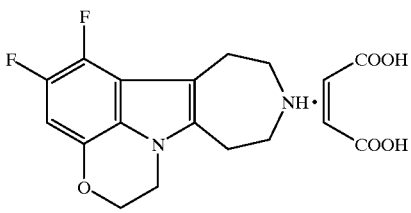

Following the general procedure of Example 20 but starting with 4,5-difluoro-2-nitrophenol, using 10% sulfuric acid in step 3, and preparing the Maleic acid salt, the title compound was obtained (mp 184–185° C.). ¹H NMR (CD₃OD) δ 6.45, 6.23, 4.46, 4.17, 3.45–3.50, 3.34–3.37, 3.220–3.24; IR (drift) 3070, 2879, 2780, 2728, 1601, 1575, 1518, 1482, 1457, 1373, 1353, 1171, 1042, 1000 cm⁻¹.

EXAMPLE 34

Preparation of 5-Chloro-6-fluoro-1,2,8,9,10,11-hexahydro-7H-azepino[4,5-b][1,4]oxazino[2,3,4-hi]indole Maleic Acid

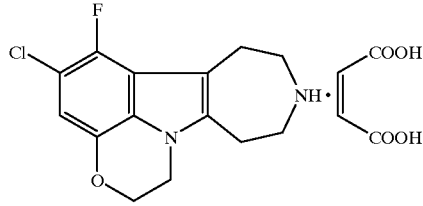

Following the general procedure of Example 20 but starting with 5-chloro-4-fluoro-2-nitrophenol, using 10% sulfuric acid in step 3, and preparing the Maleic acid salt, the title compound was obtained (mp 194–195° C.). ¹H NMR (CD₃OD) δ 6.52, 6.24, 4.46, 4.18, 3.51–3.45, 3.29–3.37, 3.21–3.25; IR (drift) 1615, 1583, 1552, 1501, 1480, 1456, 1368, 1355, 1280, 1222, 1169 cm⁻¹.

EXAMPLE 35

Preparation of 5-Fluoro-6-chloro-1,2,8,9,10,11-hexahydro-7H-azepino[4,5-b][1,4]oxazino[2,3,4-hi]indole Maleic Acid

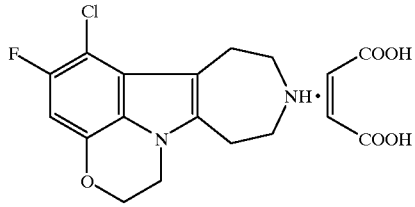

Following the general procedure of Example 20 but starting with 4-chloro-5-fluoro-2-nitrophenol, using 10% sulfuric acid in step 3, and preparing the Maleic acid salt, the title compound was obtained (mp 173–175° C.). ¹H NMR (CD₃OD) δ 6.50, 3.25, 4.50, 4.19, 3.56–3.59, 3.44–3.50, 3.22–3.25; IR (drift) 3062, 3028, 2971, 2897, 1626, 1608, 1585, 1498, 1463, 1372, 1365, 1352, 1153, 1036 cm⁻¹.

EXAMPLE 36

Preparation of 5,6-Dichloro-1,2,8,9,10,11-hexahydro-7H-azepino[4,5-b][1,4]oxazino[2,3,4-hi]indole Maleic Acid

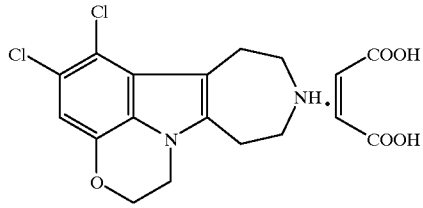

Following the general procedure of Example 20 but starting with 4,5-dichloro-2-nitrophenol, using 10% sulfuric acid in step 3, and preparing the Maleic acid salt, the title compound was obtained (mp 180–181° C.). $^1$H NMR (CD$_3$OD) δ 6.68 (s, 1 H), 6.23 (s, 2 H), 4.49 (t, J=4.4 Hz, 2 H), 4.20 (t, J=4.8 Hz, 2 H), 3.59–3.62 (t, J=2 Hz, H), 3.45–3.51 (m, 4 H), 3.22–3.26 (m, 2 H); IR (drift) 2887, 2840, 1625, 1608, 1578, 1551, 1486, 1458, 1372, 1351, 1273, 1023 cm$^{-1}$.

EXAMPLE 37

Preparation of 4,6-Dichloro-1,2,8,9,10,11-hexahydro-7H-azepino[4,5-b][1,4]oxazino[2,3,4-hi]indole Hydrochloride

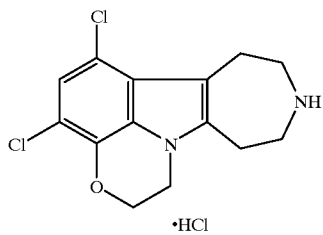

Following the general procedure of Example 20 but starting with 3,5-dichloro-2-nitrophenol, and using 10% sulfuric acid in step 3, the title compound was obtained (decompose >255° C.). $^1$H NMR (CD$_3$OD) δ 6.89, 4.55, 4.21, 3.56–3.59, 3.44–3.51, 3.23–3.27; IR (drift) 2955, 2895, 2743, 2652, 2635, 2556, 2428, 1494, 1468, 1420, 1345, 1294, 1229 cm$^{-1}$.

EXAMPLE 38

Preparation of 1-Chloro-2-fluoro-4,5,8,9,10,11-hexahydro-7H-azepino[4,5-b]pyrrolo[3,2,1-hi]indole Maleic Acid

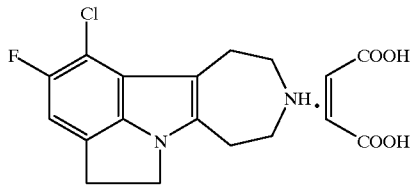

Following the general procedure outlined in EXAMPLE 14, and making non-critical variations but starting with 6-chloro-5-fluoro indoline, the title compound was obtained (amorphous solid). $^1$H NMR (CD$_3$OD) 6.70, 6.23, 4.52, 3.69, 3.34–3.22, 3.08; IR (drift) 2420 (b), 1628, 1561, 1506 (s), 1449, 1421, 1378 (s), 1350, 1337, 1323, 1300, 1291, 1278, 1254, 1147 cm$^{-1}$; MS (ESI+) for C$_{14}$H$_{14}$ClFN$_2$ m/z 265.2 (M+H)$^+$.

EXAMPLE 39

Preparation of 2-Chloro-4,5,8,9,10,11-hexahydro-7H-azepino[4,5-b]pyrrolo[3,2,1-hi]indole Maleic Acid

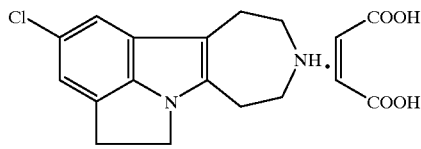

Following the general procedure outlined in EXAMPLE 14, and making non-critical variations but starting with 5-chloro-indoline, the title compound was obtained (amorphous solid). $^1$H NMR (CD$_3$OD) 7.16, 6.91, 6.81, 4.45, 3.74, 3.40, 3.24, 3.15; MS (ESI+) for C$_{14}$H$_{15}$ClN$_2$ m/z 247.2 (M+H)$^+$.

EXAMPLE 40

Preparation of 1-Chloro-4,5,8,9,10,11-hexahydro-7H-azepino[4,5-b]pyrrolo[3,2,1-hi]indole Maleic Acid

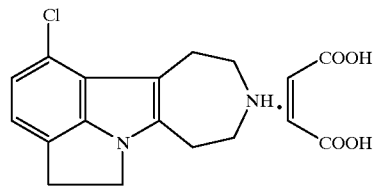

Following the general procedure outlined in EXAMPLE 14, and making non-critical variations but starting with 6-chloro-indoline, the title compound was obtained (amorphous solid). $^1$H NMR (CD$_3$OD) 6.91, 6.81, 6.77, 4.90, 3.69, 3.34, 3.21; MS (ESI+) for C$_{14}$H$_{15}$ClN$_2$ m/z 247.2 (M+H)$^+$.

EXAMPLE 41

Preparation of 5,6,9,10,11,12-hexahydro-4H,8H-azepino[4',5':4,5]pyrrolo[3,2,1-ij]quinolin-4-one oxalate

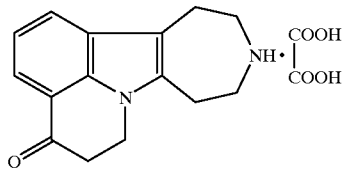

Step 7. Preparation of Ethyl 3-(3-benzoyl-2,3,4,5-tetrahydroazepino[4,5-b]indol-6(1H)-yl)propanoate.

A mixture of 3-benzoyl-1,2,3,4,5,6-hexahydroazepino[4,5-b]indole (5.00 g, 17.2 mmol), cesium carbonate (5.61 g, 17.2 mmol), and ethyl acrylate (1.90 mL, 17.5 mmol) in acetonitrile (250 mL) was heated under N$_2$ at 50° C. for 5 h (reaction can also be run in DMF at room temperature). Cooled to room temperature, diluted with H$_2$O, and extracted with EtOAc. The combined organic extracts were washed with saturated aqueous NaCl, dried over Na$_2$SO$_4$, decanted, and concentrated under reduced pressure. The crude product was purified by silica gel chromatography with EtOAc/hexanes (2: 1) to give 4.82 g (72%) of the title compound as a yellow oil. $^1$H NMR (CDCl$_3$) δ 7.57–7.38, 7.32, 7.23–7.07, 4.49–4.33, 4.20–4.02, 3.77–3.66, 3.28–3.13, 2.94, 2.72, 1.24; IR (liq.) 2981, 1731, 1631, 1467, 1445, 1422, 1381, 1368, 1349, 1319, 1295, 1272, 1242, 1187, 742, 707 cm$^{-1}$; MS (ESI) 391.0 (M$^+$+H).

Step 8. Preparation of 10-Benzoyl-5,6,9,10,11,12-hexahydro-4H,8H-azepino[4',5':4,5]pyrrolo[3,2,1-ij]quinolin-4-one.

A solution of potassium hydroxide (0.80 g, 14.3 mmol) in H$_2$O (20 mL) was added to a solution of ethyl 3-(3-benzoyl-2,3,4,5-tetrahydroazepino[4,5-b]indol-6(1H)-yl)propanoate (4.25 g, 10.9 mmol) in THF (30 mL). The reaction mixture was heated at 60° C. for 1 h, then cooled to room temperature, acidified with 10% aqueous HCl, and extracted with EtOAc. The combined organic extracts were washed with saturated aqueous NaCl, dried over Na$_2$SO$_4$, decanted, and concentrated under reduced pressure to give 3.73 g of crude acid. The crude acid (2.00 g, 5.52 mmol) was then added to neat PPA (18.6 g) stirring at 100° C. under N$_2$. After 1.5 h, the reaction was cooled to room temperature, quenched with ice and 10% aqueous NaOH, and then extracted with EtOAc. The combined organic extracts were washed with saturated aqueous NaCl, dried over Na$_2$SO$_4$, decanted, and concentrated under reduced pressure. The crude product was purified by silica gel chromatography with EtOAc/hexanes (gradient 1:1 to 2:1) to give 0.81 g (43%) of the title compound as a yellow solid (mp 177.5–181° C.). $^1$H NMR (d-DMSO) δ 7.75, 7.46, 7.09, 4.45–4.24, 3.93, 3.61, 3.34, 3.17, 3.11–2.80; IR (drift) 1676, 1628, 1587, 1493, 1483, 1466, 1428, 1357, 1324, 1295, 1276, 1266, 1191, 754, 706 cm$^1$.

Step 9. Preparation of 5,6,9,10,11,12-Hexahydro-4H,8H-azepino[4',5':4,5]pyrrolo[3,2,1-ij]quinolin-4-one Oxalate.

A solution of 10-benzoyl-5,6,9,10,11,12-hexahydro-4H, 8H-azepino[4',5':4,5]pyrrolo[3,2,1-ij]quinolin-4-one (0.20 g, 0.58 mmol) in THF/MeOH/50% aqueous NaOH (3:2:1, 9 mL) was heated under N$_2$ at reflux for 4 d. Cooled to room temperature, diluted with saturated aqueous NaCl, and extracted with CH$_2$Cl$_2$. The combined organic extracts were washed with saturated aqueous NaCl, dried over Na$_2$SO$_4$, decanted, and concentrated under reduced pressure. The crude product was purified by silica gel chromatography with CH$_2$Cl$_2$/MeOH/Et$_2$NH (gradient 95:5:0 to 95:4:1) to give 0.10 g (74%) of the free base of title compound as a dark yellow foam. The oxalate salt was prepared by treating a solution of the free base in methanol with a solution of oxalic acid in ether to give a precipitate that crystallized from methanol as small yellow needles of the title compound (mp 199–202° C. [dec.]). $^1$H NMR (d-DMSO) δ 7.78, 7.46, 7.15, 4.39, 4.19, 3.39, 3.34, 3.24, 3.14, 3.02; IR (drift) 2965, 2890, 2841, 2799, 2732, 2516, 2484, 1720, 1673, 1626, 1607, 1591, 1492, 1460, 1206 cm$^{-1}$.

EXAMPLE 42

Preparation of 2-Fluoro-5,6,9,10,11,12-hexahydro-4H,8H-azepino[4',5':4,5]pyrrolo[3,2,1-ij]quinolin-4-one Maleate

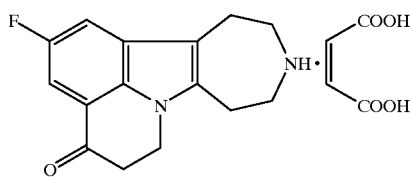

Following the general procedure of Example 41, making non-critical variations but starting with 3-benzoyl-9-fluoro-1,2,3,4,5,6-hexahydroazepino[4,5-b]indole and using maleic acid for the salt formation, the title compound was obtained (mp 242–244° C. [dec.]). $^1$H NMR (d-DMSO) δ 9.18, 7.67, 7.21, 4.40, 3.33, 3.25, 3.12, 3.04; IR (drift) 3358, 2970, 2959, 2830, 2792, 2785, 2752, 1681, 1593, 1490, 1464, 1383, 1330, 1216, 907 cm$^{-1}$.

EXAMPLE 43

Preparation of 2-chloro-5,6,9,10,11,12-hexahydro-4H,8H-azepino[4',5':4,5]pyrrolo[3,2,1-ij]quinolin-4-one oxalate

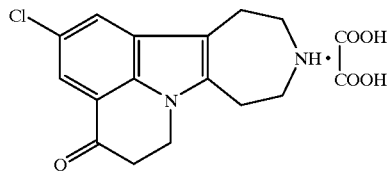

Following the general procedure of Example 41, making non-critical variations but starting with 3-benzoyl-9-chloro-1,2,3,4,5,6-hexahydroazepino[4,5-b]indole, the title compound was obtained (mp 236.5–238° C. [dec.]). $^1$H NMR (d-DMSO) δ 7.89, 7.38, 4.41, 3.69, 3.38, 3.33, 3.23, 3.13, 3.04; IR (mull) 3440, 2644, 2514, 1915, 1686, 1491, 1420, 1327, 1318, 1251, 1138, 1094, 1030, 914, 720 cm$^{-1}$.

EXAMPLE 44

Preparation of 6-Methyl-5,6,9,10,11,12-hexahydro-4H,8H-azepino[4',5':4,5]pyrrolo[3,2,1-ij]quinolin-4-one Oxalate

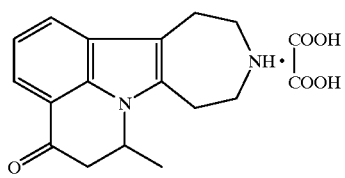

Following the general procedure of Example 41, making non-critical variations but using ethyl crotonate in step 7, the title compound was obtained (mp 215–215.5° C.). $^1$H NMR (d-DMSO) δ 7.79, 7.47, 4.97, 3.50–3.20, 3.15, 2.73, 1.16; IR (drift) 3020, 2984, 2969, 1727, 1684, 1609, 1589, 1471, 1327, 1217, 1194, 1178, 1100, 752, 706 cm$^{-1}$.

EXAMPLE 45

Preparation of 2-Fluoro-6-methyl-5,6,9,10,11,12-hexahydro-4H,8H-azepino[4',5':4,5]pyrrolo[3,2,1-ij]quinolin-4-one Oxalate

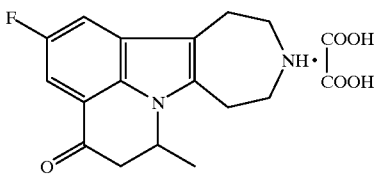

Following the general procedure of Example 41, making non-critical variations but starting with 3-benzoyl-9-fluoro-1,2,3,4,5,6-hexahydroazepino[4,5-b]indole and using ethyl crotonate in step 7, the title compound was obtained (mp 209.5–211.5° C.). $^1$H NMR (d-DMSO) δ 7.69, 7.22, 4.99, 3.44–3.22, 3.12, 2.78, 1.16; IR (drift) 2969, 1743, 1727, 1716, 1688, 1646, 1616, 1480, 1418, 1377, 1214, 1145, 1102, 858, 602 cm$^{-1}$.

EXAMPLE 46

Preparation of 2,3-Dichloro-6-methyl-5,6,9,10,11,12-hexahydro-4H,8H-azepino[4',5':4,5]pyrrolo[3,2,1-ij]quinolin-4-one Mesylate

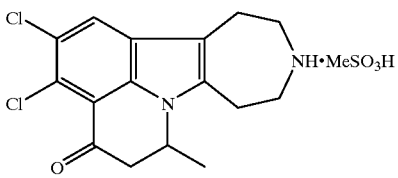

Following the general procedure of Example 41, making non-critical variations but starting with 3-benzoyl-8,9-dichloro-1,2,3,4,5,6-hexahydroazepino[4,5-b]indole, using ethyl crotonate in step 7, and using methanesulfonic acid for the salt formation, the title compound was obtained (mp 225–230° C. [dec.]). $^1$H NMR (d-DMSO) δ 8.94, 8.12, 4.97, 3.48–3.20, 3.13, 2.77, 2.30, 1.20; IR (drift) 3029, 2979, 2849, 2792, 1683, 1481, 1410, 1312, 1214, 1196, 1184, 1161, 1145, 1040, 775 cm$^{-1}$.

EXAMPLE 47

Preparation of 6-Propyl-5,6,9,10,11,12-hexahydro-4H,8H-azepino[4',5':4,5]pyrrolo[3,2,1-ij]quinolin-4-one Hydrochloride

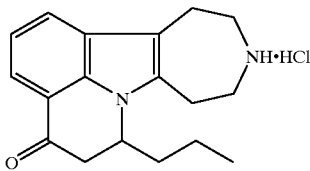

Following the general procedure of Example 41, making non-critical variations but using ethyl trans-hexenoate in step 7 and using hydrochloric acid for the salt formation, the title compound was obtained (mp 193–194.5° C.). $^1$H NMR (d-DMSO) δ 9.38, 7.79, 7.45, 7.14, 4.87, 3.54, 3.45–3.19, 3.16, 2.83, 1.47, 1.13, 0.78; IR (drift) 2957, 2926, 2870, 2853, 2741, 1683, 1588, 1471, 1416, 1354, 1325, 1279, 1191, 795, 751 cm$^{-1}$.

EXAMPLE 48

Preparation of 6-(trifluoromethyl)-5,6,9,10,11,12-Hexahydro-4H,8H-azepino[4',5':4,5]pyrrolo[3,2,1-ij]quinolin-4-one Oxalate

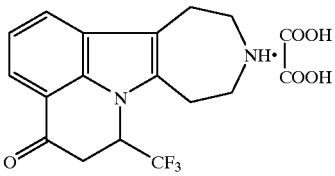

Following the general procedure of Example 41, making non-critical variations but using ethyl 4,4,4-trifluorocrotonate in step 7 and using hydrochloric acid for the salt formation, the title compound was obtained (mp 201.5–202.5° C.). $^1$H NMR (d-DMSO) δ 7.86, 7.54, 7.24, 5.94, 3.73, 3.67, 3.43–3.19, 3.16, 3.00; IR (drift) 1726, 1694, 1645, 1639, 1592, 1469, 1416, 1336, 1272, 1253, 1204, 1195, 1177, 1127, 945 cm$^{-1}$.

EXAMPLE 49

Preparation of 5,6,8,9,10,11,12,12a-Octahydro-4H,7aH-azepino[4',5':4,5]pyrrolo[3,2,1-ij]quinolin-4-ol

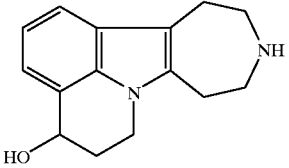

Step 10

Preparation of 10-Benzoyl-5,6,8,9,10,11,12,12a-octahydro-4H,7aH-azepino[4',5':4,5]pyrrolo[3,2,1-ij]quinolin-4-ol.

A solution of 10-benzoyl-5,6,9,10,11,12-hexahydro-4H,8H-azepino[4',5':4,5]pyrrolo[3,2,1-ij]quinolin-4-one (1.46 g, 4.24 mmol) in ethanol (40 mL) was cooled to 0° C. under N$_2$. Added sodium borohydride (0.32 g, 8.46 mmol) and allowed to warm slowly to room temperature. Concentrated under reduced pressure to approximately 10 mL, diluted with H$_2$O, and extracted with CH$_2$Cl$_2$. The combined organic extracts were washed with saturated aqueous NaCl, dried over Na$_2$SO$_4$, decanted, and concentrated under reduced pressure. The crude product was purified by silica gel chromatography with EtOAc/heptanes (2:1) to give 1.24 g (84%) of the title compound as a yellow foam. $^1$H NMR (CDCl$_3$) δ 7.42, 7.33, 7.12–7.02, 5.10, 4.13, 4.02, 3.68, 3.21, 2.92, 2.38, 2.23, 1.80; IR (drift) 1627, 1614, 1475, 1466, 1457, 1448, 1429, 1372, 1360, 1329, 1292, 1268, 785, 747, 706 cm$^{-1}$; MS (ESI) 369.1 (M$^+$+Na).

The 10-benzoyl-5,6,8,9,10,11,12,12a-octahydro-4H,7aH-azepino[4',5':4,5]pyrrolo[3,2,1-ij]quinolin-4-ol was then hydrolyzed following the procedure outlined in step 9 to give 5,6,8,9,10,11,12,12a-octahydro-4H,7aH-azepino[4',5':4,5]pyrrolo[3,2,1-ij]quinolin-4-ol as a tan foam. $^1$H NMR (CDCl₃) δ 7.43, 7.09, 5.11, 4.11, 3.16, 3.02, 2.38, 2.26; IR (drift) 3300, 3047, 2923, 2878, 2828, 2751, 1479, 1454, 1430, 1415, 1371, 1330, 1199, 1074, 746 cm⁻¹; HRMS (EI) calcd for $C_{15}H_{18}N_2O$ 242.1419, found 242.1422.

EXAMPLE 50

Preparation of 4-Methoxy-5,6,8,9,10,11,12,12a-octahydro-4H,7aH-azepino[4',5':4,5]pyrrolo[3,2,1-ij]quinoline

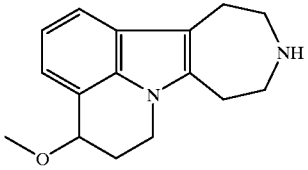

Step 11. Preparation of 10-Benzoyl-4-methoxy-5,6,8,9,10,11,12,12a-octahydro-4H,7aH-azepino[4',5':4,5]pyrrolo[3,2,1-ij]quinoline.

NaH (60% dispersion in mineral oil, 0.50 g, 1.2 mmol) was added to a solution of 10-benzoyl-5,6,8,9,10,11,12,12a-octahydro-4H,7aH-azepino[4',5':4,5]pyrrolo[3,2,1-ij]quinolin-4-ol (0.20 g, 0.58 mmol) in DMF (5.0 mL) at 0° C. under N₂. After 30 min, iodomethane (0.040 mL, 0.64 mmol) was added. The reaction was quenched with saturated aqueous NH₄Cl after 1 h and then allowed to warm to room temperature prior to extracting with EtOAc. The combined organic extracts were washed with saturated aqueous NaCl, dried over Na₂SO₄, decanted, and concentrated under reduced pressure. The crude product was purified by silica gel chromatography with EtOAc/heptanes (2:1) to give 0.16 g (79%) of the title compound as a beige foam. ¹H NMR (CDCl₃) δ 7.46–7.30, 6.94, 4.51, 4.22–4.03, 4.01–3.79, 3.65–3.41, 3.29, 3.12, 3.04, 2.90, 2.82, 2.34, 2.08; IR (drift) 1631, 1493, 1477, 1459, 1422, 1370, 1359, 1324, 1292, 1267, 1098, 1085, 786, 748, 706 cm⁻¹; HRMS (FAB) calcd for $C_{23}H_{24}N_2O_2$+H 361.1916, found 361.1913.

Following the general procedure of step 4, making non-critical variations but starting with 10-benzoyl-4-methoxy-5,6,8,9,10,11,12,12a-octahydro-4H,7aH-azepino[4',5':4,5]pyrrolo[3,2,1-ij]quinoline, the title compound was obtained as a brown oil. ¹H NMR (CDCl₃) δ 7.45, 7.07, 4.56, 4.26, 4.09, 3.42, 3.27–3.13, 3.11–2.94, 2.49, 2.18; IR (liq.) 2926, 2905, 2882, 2820, 1492, 1479, 1453, 1415, 1370, 1332, 1200, 1098, 1083, 1066, 748 cm⁻¹, HRMS (FAB) calcd for $C_{16}H_{20}N_2O$+H 257.1654, found 257.1665.

EXAMPLE 51

Preparation of 4-Phenoxy-5,6,9,10,11,12-hexahydro-4H,8H-azepino[4',5':4,5]pyrrolo[3,2,1-ij]quinoline

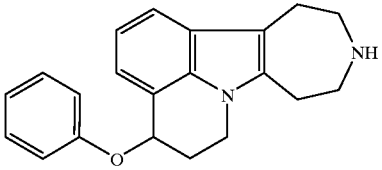

Step 12. Preparation of 10-Benzoyl-4-phenoxy-5,6,9,10,11,12-hexahydro-4H,8H-azepino[4',5':4,5]pyrrolo[3,2,1-ij]quinoline 1,1'-Azobis(N,N-dimethylformamide) (0.34 g, 2.0 mmol) was added to a solution of 10-benzoyl-5,6,8,9,10,11,12,12a-octahydro-4H,7aH-azepino[4',5':4,5]pyrrolo[3,2,1-ij]quinolin-4-ol (0.45 g, 1.3 mmol), phenol (0.18 g, 1.9 mmol), and tributylphosphine (0.49 mL, 2.0 mmol) in dry benzene (4.0 mL) at room temperature under N₂. The reaction mixture immediately congealed but resumed stirring upon heating to 60° C. After 5 h, the reaction was cooled to room temperature and filtered to remove white precipitate. The filtrate was concentrated under reduced pressure and purified by silica gel chromatography with heptanes/EtOAc (gradient 3:1 to 3:2) to give 0.26 g (47%) of the title compound as a beige foam. ¹H NMR (CDCl₃) δ 7.52–7.38, 7.32, 7.11–6.95, 5.68, 4.21–3.90, 3.69, 3.21, 2.91, 2.63, 2.34; IR (drift) 1630, 1596, 1492, 1458, 1421, 1359, 1327, 1291, 1267, 1226, 1192, 786, 750, 706, 694 cm⁻¹; MS (ESI) 423.3 (M⁺+H).

Following the general procedure of step 4, making non-critical variations but starting with 10-benzoyl-4-phenoxy-5,6,9,10,11,12-hexahydro-4H,8H-azepino[4',5':4,5]pyrrolo[3,2,1-ij]quinoline, the title compound was obtained. MS (ESI) 319.2 (M⁺+H).

EXAMPLE 52

Using synthetic procedures similar to those described herein, the following compounds of formula (I) wherein R₂ is hydrogen can also be prepared:

4-bromo-1,2,8,9,10,11-hexahydro-7H-azepino[4,5-b][1,4]oxazino[2,3,4-hi]indole (100);

5-bromo-1,2,8,9,10,11-hexahydro-7H-azepino[4,5-b][1,4]oxazino[2,3,4-hi]indole (101);

6-bromo-1,2,8,9,10,11-hexahydro-7H-azepino[4,5-b][1,4]oxazino[2,3,4-hi]indole (102);

5,6-dibromo-1,2,8,9,10,11-hexahydro-7H-azepino[4,5-b][1,4]oxazino[2,3,4-hi]indole (103);

4,6-dibromo-1,2,8,9,10,11-hexahydro-7H-azepino[4,5-b][1,4]oxazino[2,3,4-hi]indole (104);

4-methoxy-1,2,8,9,10,11-hexahydro-7H-azepino[4,5-b][1,4]oxazino[2,3,4-hi]indole (105);

5-methoxy-1,2,8,9,10,11-hexahydro-7H-azepino[4,5-b][1,4]oxazino[2,3,4-hi]indole (106);

6-methoxy-1,2,8,9,10,11-hexahydro-7H-azepino[4,5-b][1,4]oxazino[2,3,4-hi]indole (107);

4-(triflouromethyl)-1,2,8,9,10,1-hexahydro-7H-azepino[4,5-b][1,4]oxazino[2,3,4-hi]indole (108);

5-(triflouromethyl)-1,2,8,9,10,11-hexahydro-7H-azepino[4,5-b][1,4]oxazino[2,3,4-hi]indole (109);

4-benzyloxy-1,2,8,9,10,11-hexahydro-7H-azepino[4,5-b][1,4]oxazino[2,3,4-hi]indole (110);

5-benzyloxy-1,2,8,9,10,11-hexahydro-7H-azepino[4,5-b][1,4]oxazino[2,3,4-hi]indole (111);

6-benzyloxy-1,2,8,9,10,11-hexahydro-7H-azepino[4,5-b][1,4]oxazino[2,3,4-hi]indole (112);

4-fluoro-1,2,8,9,10,11-hexahydro-7H-azepino[4,5-b][1,4]thiazino[2,3,4-hi]indole (113);

5-fluoro-1,2,8,9,10,11-hexahydro-7H-azepino[4,5-b][1,4]thiazino[2,3,4-hi]indole (114);

6-fluoro-1,2,8,9,10,11-hexahydro-7H-azepino[4,5-b][1,4]thiazino[2,3,4-hi]indole (115);

4-chloro-1,2,8,9,10,11-hexahydro-7H-azepino[4,5-b][1,4]thiazino[2,3,4-hi]indole (116);

5-chloro-1,2,8,9,10,11-hexahydro-7H-azepino[4,5-b][1,4]thiazino[2,3,4-hi]indole (117);

6-chloro-1,2,8,9,10,11-hexahydro-7H-azepino[4,5-b][1,4]thiazino[2,3,4-hi]indole (118);

4,5-difluoro-1,2,8,9,10,11-hexahydro-7H-azepino[4,5-b][1,4]thiazino[2,3,4-hi]indole (119);

5,6-difluoro-1,2,8,9,10,11-hexahydro-7H-azepino[4,5-b][1,4]thiazino[2,3,4-hi]indole (120);

4,6-difluoro-1,2,8,9,10,11-hexahydro-7H-azepino[4,5-b][1,4]thiazino[2,3,4-hi]indole (121);

4-chloro-5-fluoro-1,2,8,9,10,11-hexahydro-7H-azepino[4,5-b][1,4]thiazino[2,3,4-hi]indole (122);

4-chloro-6-fluoro-1,2,8,9,10,11-hexahydro-7H-azepino[4,5-b][1,4]thiazino[2,3,4-hi]indole (123);

5-chloro-6-fluoro-1,2,8,9,10,11-hexahydro-7H-azepino[4,5-b][1,4]thiazino[2,3,4-hi]indole (124);

6-chloro-5-fluoro-1,2,8,9,10,11-hexahydro-7H-azepino[4,5-b][1,4]thiazino[2,3,4-hi]indole (125);

4-methyl-1,2,8,9,10,11-hexahydro-7H-azepino[4,5-b][1,4]thiazino[2,3,4-hi]indole (126);

5-methyl-1,2,8,9,10,11-hexahydro-7H-azepino[4,5-b][1,4]thiazino[2,3,4-hi]indole (127);

6-methyl-1,2,8,9,10,11-hexahydro-7H-azepino[4,5-b][1,4]thiazino[2,3,4-hi]indole (128);

4-methoxy-1,2,8,9,10,11-hexahydro-7H-azepino[4,5-b][1,4]thiazino[2,3,4-hi]indole (129);

5-methoxy-1,2,8,9,10,11-hexahydro-7H-azepino[4,5-b][1,4]thiazino[2,3,4-hi]indole (130);

6-methoxy-1,2,8,9,10,11-hexahydro-7H-azepino[4,5-b][1,4]thiazino[2,3,4-hi]indole; (131);

4-(triflouromethyl)-1,2,8,9,10,11-hexahydro-7H-azepino[4,5-b][1,4]thiazino[2,3,4-hi]indole (132);

5-(triflouromethyl)-1,2,8,9,10,11-hexahydro-7H-azepino[4,5-b][1,4]thiazino[2,3,4-hi]indole (133);

6-(triflouromethyl)-1,2,8,9,10,11-hexahydro-7H-azepino[4,5-b][1,4]thiazino[2,3,4-hi]indole (134);

4-benzyloxy-1,2,8,9,10,11-hexahydro-7H-azepino[4,5-b][1,4]thiazino[2,3,4-hi]indole (135);

5-benzyloxy-1,2,8,9,10,11-hexahydro-7H-azepino[4,5-b][1,4]thiazino[2,3,4-hi]indole (136);

6-benzyloxy-1,2,8,9,10,11-hexahydro-7H-azepino[4,5-b][1,4]thiazino[2,3,4-hi]indole (137);

1-fluoro-4,5,8,9,10,11-hexahydro-7H-azepino[4,5-b]pyrrolo[3,2,1-hi]indole (138);

3-fluoro-4,5,8,9,10,11-hexabydro-7H-azepino[4,5-b]pyrrolo[3,2,1-hi]indole (139);

1-bromo-4,5,8,9,10,11-hexahydro-7H-azepino[4,5-b]pyrrolo[3,2,1-hi]indole (140);

2-bromo-4,5,8,9,10,11-hexahydro-7H-azepino[4,5-b]pyrrolo[3,2,1-hi]indole (141);

3-bromo-4,5,8,9,10,11-hexahydro-7H-azepino[4,5-b]pyrrolo[3,2,1-hi]indole (142);

3-chloro-1-4,5,8,9,10,11-hexahydro-7H-azepino[4,5-b]pyrrolo[3,2,1-hi]indole (143);

2-chloro-1-fluoro-4,5,8,9,10,11-hexahydro-7H-azepino[4,5-b]pyrrolo[3,2,1-hi]indole (144);

1-methoxy-4,5,8,9,10,11-hexahydro-7H-azepino[4,5-b]pyrrolo[3,2,1-hi]indole (145);

3-methoxy-4,5,8,9,10,11-hexahydro-7H-azepino[4,5-b]pyrrolo[3,2,1-hi]indole (146);

4-methyl-4,5,8,9,10,11-hexahydro-7H-azepino[4,5-b]pyrrolo[3,2,1-hi]indole (147);

1-(trifluoromethyl)-4,5,8,9,10,11-hexahydro-7H-azepino[4,5-b]pyrrolo[3,2,1-hi]indole (148);

2-(trifluoromethyl)-4,5,8,9,10,11-hexahydro-7H-azepino[4,5-b]pyrrolo[3,2,1-hi]indole (149);

3-(trifluoromethyl)-4,5,8,9,10,11-hexahydro-7H-azepino[4,5-b]pyrrolo[3,2,1-hi]indole (150);

4-benzyloxy-5,6,8,9,10,11,12,12a-octahydro-4H,7aH-azepino[4',5':4,5]pyrrolo[3,2,1-ij]quinoline (151);

4-(3-chlorophenoxy)-5,6,9,10,11,12-hexahydro-4H,8H-azepino[4',5':4,5]pyrrolo[3,2,1-ij]quinoline (152);

4-(2-chlorophenoxy)-5,6,9,10,11,12-hexahydro-4H,8H-azepino[4',5':4,5]pyrrolo[3,2,1-ij]quinoline (153);

4-(4-methoxyphenoxy)-5,6,9,10,11,12-hexahydro-4H,8H-azepino[4',5':4,5]pyrrolo[3,2,1-ij]quinoline (154);

4-(3-methoxyphenoxy)-5,6,9,10,11,12-hexahydro-4H,8H-azepino[4',5':4,5]pyrrolo[3,2,1-ij]quinoline (155);

4-(2-methoxyphenoxy)-5,6,9,10,11,12-hexahydro-4H,8H-azepino[4',5':4,5]pyrrolo[3,2,1-ij]quinoline (156);

4-(4-bromo-2-methoxyphenoxy)-5,6,9,10,11,12-hexahydro-4H,8H-azepino[4',5':4,5]pyrrolo[3,2,1-ij]quinoline (157);

5,6,9,10,11,12-hexahydro-4H,8H-azepino[4',5':4,5]pyrrolo[3,2,1-ij]quinolin-4-amine (158);

N-phenyl-5,6,9,10,11,12-hexahydro-4H,8H-azepino[4',5':4,5]pyrrolo[3,2,1-ij]quinolin-4-amine (159);

N-(4-chlorophenyl)-5,6,9,10,11,12-hexahydro-4H,8H-azepino[4',5':4,5]pyrrolo[3,2,1-ij]quinolin-4-amine (160);

N-(3-chlorophenyl)-5,6,9,10,11,12-hexahydro-4H,8H-azepino[4',5':4,5]pyrrolo[3,2,1-ij]quinolin-4-amine (161);

N-(2-chlorophenyl)-5,6,9,10,11,12-hexahydro-4H,8H-azepino[4',5':4,5]pyrrolo[3,2,1-ij]quinolin-4-amine (162);

N-(4-methoxyphenyl)-5,6,9,10,11,12-hexahydro-4H,8H-azepino[4',5':4,5]pyrrolo[3,2,1-ij]quinolin-4-amine (163);

N-(3-methoxyphenyl)-5,6,9,10,11,12-hexahydro-4H,8H-azepino[4',5':4,5]pyrrolo[3,2,1-ij]quinolin-4-amine (164);

N-(2-methoxyphenyl)-5,6,9,10,11,12-hexahydro-4H,8H-azepino[4',5':4,5]pyrrolo[3,2,1-ij]quinolin-4-amine (165);

N-(4-bromo-2-methoxyphenyl)-5,6,9,10,11,12-hexahydro-4H,8H-azepino[4',5':4,5]pyrrolo[3,2,1-ij]quinolin-4-amine (166);

5,6,9,10,11,12-hexahydro-4H,8H-azepino[4',5':4,5]pyrrolo[3,2,1-ij]quinoline-4-thione (167);

4-(phenylsulfonyl)-5,6,9,10,11,12-hexahydro-4H,8H-azepino[4',5':4,5]pyrrolo[3,2,1-ij]quinoline (168);

4-(4-chlorophenylsulfonyl)-5,6,9,10,11,12-hexahydro-4H,8H-azepino[4',5':4,5]pyrrolo[3,2,1-ij]quinoline (169);

4-(3-chlorophenylsulfonyl)-5,6,9,10,11,12-hexahydro-4H,8H-azepino[4',5':4,5]pyrrolo[3,2,1-ij]quinoline (170);

4-(2-chlorophenylsulfonyl)-5,6,9,10,11,12-hexahydro-4H,8H-azepino[4',5':4,5]pyrrolo[3,2,1-ij]quinoline (171);

4-(4-methoxyphenylsulfonyl)-5,6,9,10,11,12-hexahydro-4H,8H-azepino[4',5':4,5]pyrrolo[3,2,1-ij]quinoline (172);

4-(3-methoxyphenylsulfonyl)-5,6,9,10,11,12-hexahydro-4H,8H-azepino[4',5':4,5]pyrrolo[3,2,1-ij]quinoline (173);

4-(2-methoxyphenylsulfonyl)-5,6,9,10,11,12-hexahydro-4H,8H-azepino[4',5':4,5]pyrrolo[3,2,1-ij]quinoline (174);

4-(4-bromo-2-methoxyphenylsulfonyl)-5,6,9,10,11,12-hexahydro-4H,8H-azepino[4',5':4,5]pyrrolo[3,2,1-ij]quinoline (175);

5,6,8,9,10,11,12,12a-octahydro-4H,7aH-azepino[4',5':4,5]pyrrolo[3,2,1-ij]quinolin-5-ol (176);

5-methoxy-5,6,8,9,10,11,12,12a-octahydro-4H,7aH-azepino[4',5':4,5]pyrrolo[3,2,1-ij]quinoline (177);

5-benzyloxy-5,6,8,9,10,11,12,12a-octahydro-4H,7aH-azepino[4',5':4,5]pyrrolo[3,2,1-ij]quinoline (178);

5-phenoxy-5,6,9,10,11,12-hexahydro-4H,8H-azepino[4',5':4,5]pyrrolo[3,2,1-ij]quinoline (179);

5-(4-chlorophenoxy)-5,6,9,10,11,12-hexahydro-4H,8H-azepino[4',5':4,5]pyrrolo[3,2,1-ij]quinoline (180);

5-(3-chlorophenoxy)-5,6,9,10,11,12-hexahydro-4H,8H-azepino[4',5':4,5]pyrrolo[3,2,1-ij]quinoline (181);

5-(2-chlorophenoxy)-5,6,9,10,11,12-hexahydro-4H,8H-azepino[4',5':4,5]pyrrolo[3,2,1-ij]quinoline (182);

5-(4-methoxyphenoxy)-5,6,9,10,11,12-hexahydro-4H,8H-azepino[4',5':4,5]pyrrolo[3,2,1-ij]quinoline (183);

5-(3-methoxyphenoxy)-5,6,9,10,11,12-hexahydro-4H,8H-azepino[4',5':4,5]pyrrolo[3,2,1-ij]quinoline (184);

5-(2-methoxyphenoxy)-5,6,9,10,11,12-hexahydro-4H,8H-azepino[4',5':4,5]pyrrolo[3,2,1-ij]quinoline (185);

5-(4-bromo-2-methoxyphenoxy)-5,6,9,10,11,12-hexahydro-4H,8H-azepino[4',5':4,5]pyrrolo[3,2,1-ij]quinoline (186);

5,6,9,10,11,12-hexahydro-4H,8H-azepino[4',5':4,5]pyrrolo[3,2,1-ij]quinolin-5-amine (187);

N-phenyl-5,6,9,10,11,12-hexahydro-4H,8H-azepino[4',5':4,5]pyrrolo[3,2,1-ij]quinolin-5-amine (188);

N-(4-chlorophenyl)-5,6,9,10,11,12-hexahydro-4H,8H-azepino[4',5':4,5]pyrrolo[3,2,1-ij]quinolin-5-amine (189);

N-(3-chlorophenyl)-5,6,9,10,11,12-hexahydro-4H,8H-azepino[4',5':4,5]pyrrolo[3,2,1-ij]quinolin-5-amine (190);

N-(2-chlorophenyl)-5,6,9,10,11,12-hexahydro-4H,8H-azepino[4',5':4,5]pyrrolo[3,2,1-ij]quinolin-5-amine (191);

N-(4-methoxyphenyl)-5,6,9,10,11,12-hexahydro-4H,8H-azepino[4',5':4,5]pyrrolo[3,2,1-ij]quinolin-5-amine (192);

N-(3-methoxyphenyl)-5,6,9,10,11,12-hexahydro-4H,8H-azepino[4',5':4,5]pyrrolo[3,2,1-ij]quinolin-5-amine (193);

N-(2-methoxyphenyl)-5,6,9,10,11,12-hexahydro-4H,8H-azepino[4',5':4,5]pyrrolo[3,2,1-ij]quinolin-5-amine (194);

N-(4-bromo-2-methoxyphenyl)-5,6,9,10,11,12-hexahydro-4H,8H-azepino[4',5':4,5]pyrrolo[3,2,1-ij]quinolin-5-amine (195);

5,6,9,10,11,12-hexahydro-4H,8H-azepino[4',5':4,5]pyrrolo[3,2,1-ij]quinoline-5-thione (196);

5-(phenylsulfonyl)-5,6,9,10,11,12-hexahydro-4H,8H-azepino[4',5':4,5]pyrrolo[3,2,1-ij]quinoline (197);

5-(4-chlorophenylsulfonyl)-5,6,9,10,11,12-hexahydro-4H,8H-azepino[4',5':4,5]pyrrolo[3,2,1-ij]quinoline (198);

5-(3-chlorophenylsulfonyl)-5,6,9,10,11,12-hexahydro-4H,8H-azepino[4',5':4,5]pyrrolo[3,2,1-ij]quinoline (199);

5-(2-chlorophenylsulfonyl)-5,6,9,10,11,12-hexahydro-4H,8H-azepino[4',5':4,5]pyrrolo[3,2,1-ij]quinoline (200);

5-(4-methoxyphenylsulfonyl)-5,6,9,10,11,12-hexahydro-4H,8H-azepino[4',5':4,5]pyrrolo[3,2,1-ij]quinoline (201);

5-(3-methoxyphenylsulfonyl)-5,6,9,10,11,12-hexahydro-4H,8H-azepino[4',5':4,5]pyrrolo[3,2,1-ij]quinoline (202);

5-(2-methoxyphenylsulfonyl)-5,6,9,10,11,12-hexahydro-4H,8H-azepino[4',5':4,5]pyrrolo[3,2,1-ij]quinoline (203);

5-(4-bromo-2-methoxyphenylsulfonyl)-5,6,9,10,11,12-hexahydro-4H,8H-azepino[4',5':4,5]pyrrolo[3,2,1-ij]quinoline (204);

4-(4-chlorophenoxy)-5,6,9,10,11,12-hexahydro-4H,8H-azepino[4',5':4,5]pyrrolo[3,2,1-ij]quinoline (205);

1-[2-(4-fluorophenoxy)ethoxy]-5,6,9,10,11,12-hexahydro-4H,8H-azepino[4',5':4,5]pyrrolo[3,2,1-ij]quinoline (206);

1-[2-(3-fluorophenoxy)ethoxy]-5,6,9,10,11,12-hexahydro-4H,8H-azepino[4',5':4,5]pyrrolo[3,2,1-ij]quinoline (207);

1-[2-(2-fluorophenoxy)ethoxy]-5,6,9,10,11,12-hexahydro-4H,8H-azepino[4',5':4,5]pyrrolo[3,2,1-ij]quinoline (208);

1-[2-(4-chlorophenoxy)ethoxy]-5,6,9,10,11,12-hexahydro-4H,8H-azepino[4',5':4,5]pyrrolo[3,2,1-ij]quinoline (209);

1-[2-(3-chlorophenoxy)ethoxy]-5,6,9,10,11,12-hexahydro-4H,8H-azepino[4',5':4,5]pyrrolo[3,2,1-ij]quinoline (210);

1-[2-(2-chlorophenoxy)ethoxy]-5,6,9,10,11,12-hexahydro-4H,8H-azepino[4',5':4,5]pyrrolo[3,2,1-ij]quinoline (211);

1-[2-(4-bromophenoxy)ethoxy]-5,6,9,10,11,12-hexahydro-4H,8H-azepino[4',5':4,5]pyrrolo[3,2,1-ij]quinoline (212);

1-[2-(3-bromophenoxy)ethoxy]-5,6,9,10,11,12-hexahydro-4H,8H-azepino[4',5':4,5]pyrrolo[3,2,1-ij]quinoline (213);

1-[2-(2-bromophenoxy)ethoxy]-5,6,9,10,11,12-hexahydro-4H,8H-azepino[4',5':4,5]pyrrolo[3,2,1-ij]quinoline (214);

1-[2-(4-methoxyphenoxy)ethoxy]-5,6,9,10,11,12-hexahydro-4H,8H-azepino[4',5':4,5]pyrrolo[3,2,1-ij]quinoline (215);

1-[2-(3-methoxyphenoxy)ethoxy]-5,6,9,10,11,12-hexahydro-4H,8H-azepino[4',5':4,5]pyrrolo[3,2,1-ij]quinoline (216);

1-[2-(2-methoxyphenoxy)ethoxy]-5,6,9,10,11,12-hexahydro-4H,8H-azepino[4',5':4,5]pyrrolo[3,2,1-ij]quinoline (217);

1-[2-(4-methylphenoxy)ethoxy]-5,6,9,10,11,12-hexahydro-4H,8H-azepino[4',5':4,5]pyrrolo[3,2,1-ij]quinoline (218);

1-[2-(3-methylphenoxy)ethoxy]-5,6,9,10,11,12-hexahydro-4H,8H-azepino[4',5':4,5]pyrrolo[3,2,1-ij]quinoline (219);

1-[2-(2-methylphenoxy)ethoxy]-5,6,9,10,11,12-hexahydro-4H,8H-azepino[4',5':4,5]pyrrolo[3,2,1-ij]quinoline (220);

1-[2-(1-naphthyloxy)ethoxy]-5,6,9,10,11,12-hexahydro-4H,8H-azepino[4',5':4,5]pyrrolo[3,2,1-ij]quinoline (221);

1-[2-(2-naphthyloxy)ethoxy]-5,6,9,10,11,12-hexahydro-4H,8H-azepino[4',5':4,5]pyrrolo[3,2,1-ij]quinoline (222);

1-[2-([1,1'-biphenyl]-4-yloxy)ethoxy]-5,6,9,10,11,12-hexahydro-4H,8H-azepino[4',5':4,5]pyrrolo[3,2,1-ij]quinoline (223);

1-[2-([1,1'-biphenyl]-3-yloxy)ethoxy]-5,6,9,10,11,12-hexahydro-4H,8H-azepino[4',5':4,5]pyrrolo[3,2,1-ij]quinoline (224);

1-[2-([1,1'-biphenyl]-2-yloxy)ethoxy]-5,6,9,10,11,12-hexahydro-4H,8H-azepino[4',5':4,5]pyrrolo[3,2,1-ij]quinoline (225);

1-{2-[4-(trifluoromethoxy)phenoxy]ethoxy}-5,6,9,10,11,12-hexahydro-4H,8H-azepino[4',5':4,5]pyrrolo[3,2,1-ij]quinoline (226);

1-{2-[3-(trifluoromethoxy)phenoxy]ethoxy}-5,6,9,10,11,12-hexahydro-4H,8H-azepino[4',5':4,5]pyrrolo[3,2,1-ij]quinoline (227);

1-{2-[2-(trifluoromethoxy)phenoxy]ethoxy}-5,6,9,10,11,12-hexahydro-4H,8H-azepino[4',5':4,5]pyrrolo[3,2,1-ij]quinoline (228);

1-{2-[4-(trifluoromethyl)phenoxy]ethoxy}-5,6,9,10,11,12-hexahydro-4H,8H-azepino[4',5':4,5]pyrrolo[3,2,1-ij]quinoline (229);

1-{2-[3-(trifluoromethyl)phenoxy]ethoxy}-5,6,9,10,11,12-hexahydro-4H,8H-azepino[4',5':4,5]pyrrolo[3,2,1-ij]quinoline (230); and 1-{2-[2-(trifluoromethyl)phenoxy]ethoxy}-5,6,9,10,11,12-hexahydro-4H,8H-azepino[4',5':4,5]pyrrolo[3,2,1-ij]quinoline (231).

EXAMPLE 53

Using synthetic procedures similar to those described herein, the following compounds of formula (I) wherein $R_2$ is a protecting group can also be prepared:

benzyl 5,6,8,9,11,12-hexahydro-4H,10H-azepino[4',5':4,5]pyrrolo[3,2,1-ij]quinoline-10-carboxylate;

benzyl 2-methyl-5,6,8,9,11,12-hexahydro-4H,10H-azepino[4',5':4,5]pyrrolo[3,2,1-ij]quinoline-10-carboxylate;

10-benzoyl-1-methoxy-5,6,9,10,11,12-hexahydro-4H,8H-azepino[4',5':4,5]pyrrolo[3,2,1-ij]quinoline;

benzyl 2-fluoro-5,6,8,9,11,12-hexahydro-4H,10H-azepino[4',5':4,5]pyrrolo[3,2,1-ij]quinoline-10-carboxylate;

benzyl 6-methyl-5,6,8,9,11,12-hexahydro-4H,10H-azepino[4',5':4,5]pyrrolo[3,2,1-ij]quinoline-10-carboxylate;

benzyl 5-methyl-5,6,8,9,11,12-hexahydro-4H,10H-azepino[4',5':4,5]pyrrolo[3,2,1-ij]quinoline-10-carboxylate;

benzyl 4-methyl-5,6,8,9,11,12-hexahydro-4H,10H-azepino[4',5':4,5]pyrrolo[3,2,1-ij]quinoline-10-carboxylate;

(+)-benzyl 6-methyl-5,6,8,9,11,12-hexahydro-4H,10H-azepino[4',5':4,5]pyrrolo[3,2,1-ij]quinoline-10-carboxylate;

(−)-benzyl 6-methyl-5,6,8,9,11,12-hexahydro-4H,10H-azepino[4',5':4,5]pyrrolo[3,2,1-ij]quinoline-10-carboxylate;

(+)-benzyl 5-methyl-5,6,8,9,11,12-hexahydro-4H,10H-azepino[4',5':4,5]pyrrolo[3,2,1-ij]quinoline-10-carboxylate;

(−)-benzyl 5-methyl-5,6,8,9,11,12-hexahydro-4H,10H-azepino[4',5':4,5]pyrrolo[3,2,1-ij]quinoline-10-carboxylate;

(+)-benzyl 4-methyl-5,6,8,9,11,12-hexahydro-4H,10H-azepino[4',5':4,5]pyrrolo[3,2,1-ij]quinoline-10-carboxylate;

(−)-benzyl 4-methyl-5,6,8,9,11,12-hexahydro-4H,10H-azepino[4',5':4,5]pyrrolo[3,2,1-ij]quinoline-10-carboxylate;

benzyl 2-methyl-1,2,7,8,10,11-hexahydro-9H-azepino[4,5-b][1,4]oxazino[2,3,4-hi]indole-9-carboxylate;

benzyl 2,2-dimethyl-1,2,7,8,10,11-hexahydro-9H-azepino[4,5-b][1,4]oxazino[2,3,4-hi]indole-9-carboxylate;

benzyl 4-fluoro-1,2,7,8,10,11-hexahydro-9H-azepino[4,5-b][1,4]oxazino[2,3,4-hi]indole-9-carboxylate;

benzyl 4-chloro-1,2,7,8,10,11-hexahydro-9H-azepino[4,5-b][1,4]oxazino[2,3,4-hi]indole-9-carboxylate;

benzyl 5-fluoro-1,2,7,8,10,11-hexahydro-9H-azepino[4,5-b][1,4]oxazino[2,3,4-hi]indole-9-carboxylate;

benzyl 5-chloro-1,2,7,8,10,11-hexahydro-9H-azepino[4,5-b][1,4]oxazino[2,3,4-hi]indole-9-carboxylate;

benzyl 5-methyl-1,2,7,8,10,11-hexahydro-9H-azepino[4,5-b][1,4]oxazino[2,3,4-hi]indole-9-carboxylate;

benzyl 6-fluoro-1,2,7,8,10,11-hexahydro-9H-azepino[4,5-b][1,4]oxazino[2,3,4-hi]indole-9-carboxylate;

benzyl 6-chloro-1,2,7,8,10,11-hexahydro-9H-azepino[4,5-b][1,4]oxazino[2,3,4-hi]indole-9-carboxylate;

benzyl 6-methyl-1,2,6b,7,8,10,11,11a-octahydro-9H-azepino[4,5-b][1,4]oxazino[2,3,4-hi]indole-9-carboxylate;

benzyl 6-(trifluoromethyl)-1,2,7,8,10,11-hexahydro-9H-azepino[4,5-b][1,4]oxazino[2,3,4-hi]indole-9-carboxylate;

benzyl 5,6-difluoro-1,2,7,8,10,11-hexahydro-9H-azepino[4,5-b][1,4]oxazino[2,3,4-hi]indole-9-carboxylatebenzyl;

benzyl 5-chloro-6-fluoro-1,2,7,8,10,11-hexahydro-9H-azepino[4,5-b][1,4]oxazino[2,3,4-hi]indole-9-carboxylate;

benzyl 5-fluoro-6-chloro-1,2,7,8,10,11-hexahydro-9H-azepino[4,5-b][1,4]oxazino[2,3,4-hi]indole-9-carboxylate;

benzyl 5,6-dichloro-1,2,7,8,10,11-hexahydro-9H-azepino[4,5-b][1,4]oxazino[2,3,4-hi]indole-9-carboxylate;

benzyl 4,6-dichloro-1,2,7,8,10,11-hexahydro-9H-azepino[4,5-b][1,4]oxazino[2,3,4-hi]indole-9-carboxylate;

7-benzoyl 4,5,8,9,10,11-hexahydro-7H-azepino[4,5-b]pyrrolo[3,2,1-hi]indole;

7-benzoyl 2-fluoro-4,5,8,9,10,11-hexahydro-7H-azepino[4,5-b]pyrrolo[3,2,1-hi]indole;

7-benzoyl 2-methoxy-4,5,8,9,10,11-hexahydro-7H-azepino[4,5-b]pyrrolo[3,2,1-hi]indole;

benzyl-5-methyl-4,5,8,9,10,11-hexahydro-7H-azepino[4,5-b]pyrrolo[3,2,1-hi]-7-carboxylate;

benzyl-4,5-dimethyl-4,5,8,9,10,11-hexahydro-7H-azepino[4,5-b]pyrrolo[3,2,1-hi]indole-7-carboxylate;

benzyl-2,3,4,5,8b,9,10,11,12,12a-decahydro-1H-azepino[4',5':4,5]pyrrolo[3,2,1-jk]carbazole-7-carboxylate;

benzyl-1-chloro-2-fluoro-4,5,8,9,10,11-hexahydro-7H-azepino[4,5-b]pyrrolo[3,2,1-hi]indole-7-carboxylate;

benzyl-2-chloro-4,5,8,9,10,11-hexahydro-7H-azepino[4,5-b]pyrrolo[3,2,1-hi]indole-7-carboxylate;

benzyl-1-chloro-4,5,8,9,10,11-hexahydro-7H-azepino[4, 5-b]pyrrolo[3,2,1-hi]indole-7-carboxylate;

10-benzoyl-5,6,9,10,11,12-hexahydro-4H,8H-azepino[4', 5':4,5]pyrrolo[3,2,1-ij]quinolin-4-one;

10-benzoyl-2-fluoro-5,6,9,10,11,12-hexahydro-4H,8H-azepino[4',5':4,5]pyrrolo[3,2,1-ij]quinolin-4-one;

10-benzoyl-2-chloro-5,6,9,10,11,12-hexahydro-4H,8H-azepino[4',5':4,5]pyrrolo[3,2,1-ij]quinolin-4-one;

10-benzoyl-6-methyl-5,6,9,10,11,12-hexahydro-4H,8H-azepino[4',5':4,5]pyrrolo[3,2,1-ij]quinolin-4-one;

10-benzoyl-2-fluoro-6-methyl-5,6,9,10,11,12-hexahydro-4H,8H-azepino[4',5':4,5]-pyrrolo[3,2,1-ij]quinolin-4-one;

10-benzoyl-2,3-dichloro-6-methyl-5,6,9,10,11,12-hexahydro-4H,8H-azepino[4',5':4,5]pyrrolo[3,2,1-ij]quinolin-4-one; 10-benzoyl-6-propyl-5,6,9,10,11,12-hexahydro-4H,8H-azepino[4',5':4,5]pyrrolo[3,2,1-ij]quinolin-4-one;

10-benzoyl-6-(trifluoromethyl)-5,6,9,10,11,12-hexahydro-4H,8H-azepino[4',5':4,5]pyrrolo[3,2,1-ij]quinolin-4-one;

10-benzoyl-5,6,8,9,10,11,12,12a-octahydro-4H,7aH-azepino[4',5':4,5]pyrrolo[3,2,1-ij]quinolin-4-ol; and 10-benzoyl-4-methoxy-5,6,8,9,10,11,12,12a-octahydro-4H,7aH-azepino[4',5':4,5]pyrrolo[3,2,1-ij]quinoline.

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

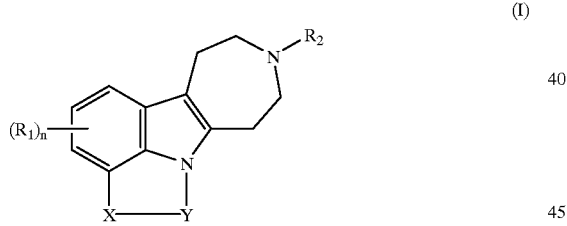

(I)

wherein each $R_1$ is independently hydroxy, nitro, halo, cyano, trifluoromethyl, tifluoromethoxy, $C_{1-7}$alkyl, $C_{1-7}$alkoxy, $C_{1-7}$alkanoyl, $C_{1-7}$alkoxycarbonyl, $C_{1-7}$alkanoyloxy, aryl, heteroaryl, —S(O)$_m$NR$_a$R$_b$, NR$_c$R$_d$, —S(O)$_m$R$_e$, or —C(=O)NR$_a$R$_b$, wherein any $C_{1-7}$alkyl, $C_{1-7}$alkoxy, $C_{1-7}$alkanoyl, $C_{1-7}$alkoxycarbonyl, or $C_{1-7}$alkanoyloxy of $R_1$ is optionally partially unsaturated and is optionally substituted with aryl, aryloxy, heteroaryl, heteroaryloxy, hydroxy, nitro, balo, cyano, $C_{1-7}$alkoxy, $C_{1-7}$alkanoyl, $C_{1-7}$alkoxycarbonyl, $C_{1-7}$alkanoyloxy, —S(O)$_m$R$_e$, —S(O)$_m$NR$_a$R$_b$, NR$_c$R$_d$, or —C(=O)NR$_a$R$_b$;

$R_2$ is hydrogen, $C_{1-7}$alkyl, $C_{1-7}$alkanoyl, arylcarbonyl, aryl, (aryl)$C_{1-7}$alkyl, $C_{1-7}$alkoxycarbonyl, aryloxycarbonyl, arylsulfonyl, or (aryl)$C_{1-7}$ alkoxycarbonyl;

X and Y together are a 2 or 3 membered saturated or partially unsaturated chain comprising one or more carbon atoms and one oxy (—O—), thio (—S—), sulfinyl (—SO—), sulfonyl (S(O)$_2$—), or NR$_f$ in the chain; wherein the chain is optionally substituted on each carbon with oxo (=O), thioxo (=S), —NR$_q$R$_r$, —S(O)$_p$R$_s$, or —OR$_t$, or with one or two substitutents independently selected from the group consisting of $C_{1-7}$alkyl, ($C_{1-7}$alkoxy)$C_{1-7}$alkyl, aryl, (aryl)$C_{1-7}$alkyl, heteroaryl, heteroaryl)$C_{1-7}$alkyl, and (aryl)oxy$C_{1-7}$ alkyl; or wherein the chain is optionally substituted on a carbon with a 4, 5, or 6 membered spirocyclic carbon ring; or wherein the chain is optionally substituted on two adjacent atoms with a 2, 3, or 4 membered alkylene chain forming a ring that is fused to the ring comprising X and Y;

each m is independently 0, 1, or 2;

n is 0, 1, 2, or 3;

p is 0, 1, or 2;

each $R_a$ and $R_b$ is independently hydrogen, $C_{1-7}$alkyl, aryl, (aryl)$C_{1-7}$alkyl, heteroaryl, or (heteroaryl)$C_{1-7}$ alkyl; or $R_a$ and $R_b$ together with the nitrogen to which they are attached form a pyrrolidino, piperidino, morpholino, or thiomorpholino ring;

each $R_c$ and $R_d$ is independently hydrogen, $C_{1-7}$alkyl, $C_{1-7}$alkanoyl, $C_{1-7}$alkoxycarbonyl, aryl, (aryl)$C_{1-7}$ alkyl, heteroaryl, (heteroaryl)$C_{1-7}$alkyl, arylcarbonyl, heteroarylcarbonyl, aryloxycarbonyl, or heteroaryloxycarbonyl; or $R_c$ and $R_d$ together with the nitrogen to which they are attached form a pyrrolidino, piperidino, morpholino, or thiomorpholino ring;

each $R_e$ is independently hydrogen, $C_{1-7}$alkyl, aryl, (aryl)$C_{1-7}$alkyl, heteroaryl, or (heteroaryl)$C_{1-7}$alkyl;

$R_f$ is hydrogen, $C_{1-7}$alkyl, aryl, (aryl)$C_{1-7}$alkyl, heteroaryl, (heteroaryl)$C_{1-7}$alkyl, or is a bond to a 2, 3, or 4 membered alkylene chain that forms a ring that is fused to the ring comprising X and Y;

each $R_q$ and $R_r$ is independently hydrogen, $C_{1-7}$alkyl, (aryl)$C_{1-7}$alkyl, heteroaryl, or (heteroaryl)$C_{1-7}$alkyl; or $R_q$ and $R_r$ together with the nitrogen to which they are attached form a pyrrolidino, piperidino, morpholino, or thiomorpholino ring;

$R_s$ is $C_{1-7}$alkyl, aryl, (aryl)$C_{1-7}$alkyl, heteroaryl, or (heteroaryl)$C_{1-7}$alkyl; and $R_t$ is hydrogen, $C_{1-7}$alkyl, aryl, (aryl)$C_{1-7}$alkyl, heteroaryl, or (heteroaryl)$C_{1-7}$alkyl; wherein any aryl or heteroaryl ring of $R_1$, $R_2$, X, Y, $R_a$–$R_f$, or $R_q$–$R_t$ is optionally substituted with one or more (e.g. 1, 2, 3, or 4) substituents independently selected from halo, hydroxy, cyano, nitro, trifluoromethyl, trifluoromethoxy, $C_{1-7}$alkyl, $C_{1-7}$alkoxy, phenyl, sulfonyl, NR$_j$R$_k$, or —C(=O)NR$_j$R$_k$; wherein each $R_j$ and $R_k$ is in independently hydrogen, $C_{1-7}$alkyl, $C_{1-7}$alkanoyl, $C_{1-7}$alkoxycarbonyl, aryl, (aryl)$C_{1-7}$ alkyl, arylcarbonyl, or aryloxycarbonyl; or $R_j$ and $R_k$ together with the nitrogen to which they are attached form a pyrrolidino, piperidino, morpholino, or thiomorpholino ring; and wherein any heteroaryl is a radical of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl or benzyl, or a radical of an ortho-fused bicyclic heterocycle of about eight to ten ring atoms derived therefrom;

or a pharmaceutically acceptable salt thereof;

provided Y is not oxy, thio, sulfinyl, or NR$_f$; and provided X and Y together are not a 2-membered unsaturated chain; and provided no carbon of X and Y is bonded to more than one oxy, thio, sulfinyl, or $NR_f$.

2. The compound of claim 1 wherein each $R_1$ is independently hydroxy, nitro, halo, cyano, trifluoromethyl, trifluoromethoxy, ($C_{1-7}$alkyl, $C_{1-7}$alkoxy, $C_{1-7}$alkanoyl, $C_{1-7}$alkoxycarbonyl, $C_{1-7}$alkanoyloxy, aryl, heteroaryl, —S(O)$_m$$NR_aR_b$, $NR_cR_d$, —S(O)$_m$$R_e$ or —C(=O)$NR_aR_b$, wherein any $C_{1-7}$alkyl, $C_{1-7}$alkoxy, $C_{1-7}$alkanoyl, $C_{1-7}$alkoxycarbonyl, or $C_{1-7}$alkanoyloxy of $R_1$ is optionally substituted with aryl, aryloxy, heteroaryl, heteroaryloxy, hydroxy, nitro, halo, cyano, $C_{1-7}$alkoxy, $C_{1-7}$alkanoyl, $C_{1-7}$alkoxycarbonyl, $C_{1-7}$alkanoyloxy, —S(O)$_m$$R_e$, —S(O)$_m$$NR_aR_b$, $NR_cR_d$, or —C(=O)$NR_aR_b$.

3. The compound of claim 1 wherein each $R_1$ is independently hydroxy, nitro, halo, cyano, trifluoromethyl, trifluorometoxy, $C_{1-7}$alkyl, $C_{1-7}$alkoxy, $C_{1-7}$alkanoyl, $C_{1-7}$alkoxycarbonyl, $C_{1-7}$alkanoyloxy, aryl, heteroaryl, —S(O)$_m$$NR_aR_b$, $NR_cR_d$, —S(O)$_m$$R_e$, or —C(=O)$NR_aR_b$, wherein any $C_{1-7}$alkyl or $C_{1-7}$alkoxy of $R_1$ is optionally substituted with aryl, aryloxy, heteroaryl, heteroaryloxy, hydroxy, nitro, halo, cyano, $C_{1-7}$alkoxy, $C_{1-7}$alkanoyl, $C_{1-7}$alkoxycarbonyl, $C_{1-7}$alkanoyloxy, —S(O)$_m$$R_e$, —S(O)$_m$$NR_aR_b$, $NR_cR_d$, or —C(=O)$NR_aR_b$.

4. The compound or claim 1 wherein each $R_1$ is independently hydroxy, nitro, halo, cyano, trifluoromethyl, trifluoromethoxy, $C_{1-7}$alkyl, $C_{1-7}$alkoxy, $C_{1-7}$alkanoyl, $C_{1-7}$alkoxycarbonyl, $C_{1-7}$alkanoyloxy, aryl, heteroaryl, —S(O)$_m$$NR_aR_b$, $NR_cR_d$, —S(O)$_m$$R_e$, or —C(=O)$NR_aR_b$, wherein any $C_{1-7}$alkyl is optionally substituted with aryl, aryloxy, heteroaryl, heteroaryloxy, hydroxy, nitro, halo, cyano, $C_{1-7}$alkoxy, $C_{1-7}$alkanoyl, $C_{1-7}$alkoxycarbonyl, $C_{1-7}$alkanoyloxy, —S(O)$_m$$R_e$, —S(O)$_m$$NR_aR_b$, $NR_cR_d$, or —C(=O)$NR_aR_b$.

5. The compound of claim 1 wherein each $R_1$ is independently hydroxy, nitro, halo, cyano, trifluoromethyl, trifluoromethoxy, $C_{1-7}$alkyl, $C_{1-7}$alkoxy, $C_{1-7}$alkanoyl, $C_{1-7}$alkoxycarbonyl, $C_{1-7}$alkanoyloxy, aryl, heteroaryl, —S(O)$_m$$NR_aR_b$, $NR_cR_d$, —S(O)$R_m$$R_e$, or —C(=O)$NR_aR_b$.

6. The compound of claim 1 wherein each $R_1$ is independently $C_{1-7}$alkyl, $C_{1-7}$alkoxy, trifluoromethyl, or halo.

7. The compound of claim 1 wherein n is 1 and $R_1$ is $C_{1-7}$alkyl, $C_{1-7}$alkoxy, or halo.

8. The compound of claim 1 wherein n is 1 and $R_1$ is methyl, methoxy, chloro, or fluoro.

9. The compound of claim 1 wherein $R_2$ is hydrogen.

10. The compound of claim 1 wherein n is 1, 2, or 3.

11. The compound of claim 1 wherein n is 0.

12. The compound of claim 1 wherein X and Y together are a 2 or 3 membered saturated or partially unsaturated chain comprising one or more carbon atoms and one oxy (—O—), thio (—S—), sulfinyl (—SO—), sulfonyl (—S(O)$_2$—), or $NR_f$ in the chain; wherein the chain is optionally substituted on each carbon with oxo (=O), thioxo (S=), —$NR_qR_r$, —S(O)$_p$$R_s$, or —$OR_t$, or with one or two substituents independently selected from the group consisting of $C_{1-7}$alkyl, ($C_{1-7}$alkoxy)$C_{1-7}$alkyl, aryl, (aryl)$C_{1-7}$alkyl, heteroaryl, (heteroaryl)$C_{1-7}$alkyl, and (aryl)oxy$C_{1-7}$alkyl.

13. The compound of claim 1 wherein X and Y together are a 2 or 3 membered saturated or partially unsaturated chain comprising one or more carbon atoms and one oxy (—O—), thio (—S—), sulfinyl (—SO—), sulfonyl (S(O)$_2$—), or $NR_f$ in the chain; wherein the chain is optionally substituted on each carbon with oxo (=O), thioxo (=S), —$NR_qR_r$, —S(O)$_p$$R_s$, or —$OR_t$.

14. The compound of claim 1 wherein X and Y together are a 2 or 3 membered saturated or partially unsaturated chain comprising one or more carbon atoms and one oxy (—O—), thio (—S—), sulfinyl (—SO—), sulfonyl (S(O)$_2$—), or $NR_f$ in the chain; wherein the chain is optionally substituted on each carbon with one or two substituents independently selected from the group consisting of $C_{1-7}$alkyl, ($C_{1-7}$alkoxy)$C_{1-7}$alkyl aryl, (aryl)$C_{1-7}$alkyl, heteroaryl, (heteroaryl)$C_{1-7}$alkyl, and (aryl)oxy$C_{1-7}$alkyl.

15. The compound of claim 1 wherein X and Y together are a 2 or 3 membered chain comprising one or more carbon atoms and one oxy, thio, sulfinyl, sulfonyl, or $NR_f$ in the chain; wherein the chain is optionally substituted on each carbon with oxo (=O), hydroxy, (aryl)oxy, heteroaryl(oxy) or $C_{1-7}$alkoxy, or with one or two substituents independently selected from the group consisting of $C_{1-7}$alkyl, ($C_{1-7}$alkoxy)$C_{1-7}$alkyl, aryl, (aryl)$C_{1-7}$alkyl, heteroaryl, (heteroaryl)$C_{1-7}$alkyl, and (aryl)oxy$C_{1-7}$alkyl; and wherein the chain is optionally substituted on two adjacent atoms with a 2, 3, or 4 membered alkylene chain forming a ring that is fused to the ring comprising X and Y.

16. The compound of claim 1 wherein X is —O—, —S—, or —C($R_g$)($R_h$)—, wherein $R_g$ and $R_h$ are each independently hydrogen, $C_{1-7}$alkyl, ($C_{1-7}$alkoxy)$C_{1-7}$alkyl, aryl, (aryl)$C_{1-7}$alkyl, heteroaryl, (heteroaryl)$C_{1-7}$alkyl or (aryl)oxy$C_{1-7}$alkyl, or $R_g$ and $R_h$ together are oxo.

17. The compound of claim 1 wherein Y is —C($R_g$)($R_h$)—, —C($R_g$)($R_h$)C($R_g$)($R_h$)—, —C($R_g$)($R_h$)C(=O)—, or —C(=O)C($R_g$)($R_h$)—, and each $R_g$ and $R_h$ is independently hydrogen or $C_{1-7}$alkyl.

18. The compound of claim 1 wherein X is —O— or —S—; and Y is —C($R_g$)($R_h$)C(=O)—, or —C($R_g$)($R_h$)C($R_g$)($R_h$)—, wherein each $R_g$ and $R_h$ is independently hydrogen or $C_{1-7}$alkyl.

19. The compound of claim 1 wherein X is —O— or —S—; and Y is —C($R_g$)($R_h$)C(=O)—, —C(=O)C($R_g$)($R_h$)—, or —C($R_g$)($R_h$)C($R_g$)($R_h$)—, wherein each $R_g$ and $R_h$ is independently hydrogen or $C_{1-7}$alkyl.

20. The compound of claim 1 wherein X and Y together are —O—CH$_2$CH$_2$—, —S—CH$_2$CH$_2$—, —S(O)—CH$_2$CH$_2$—, —S(O)$_2$—CH$_2$CH$_2$—, —NR$_f$—CH$_2$CH$_2$—, —CH$_2$OC(=O)—, or —OCH$_2$C(=O)—; wherein each $R_g$ is independently —$NR_qR_r$, —S(O)$_p$$R_s$, or —$OR_t$.

21. The compound of claim 1 wherein X and Y together are —O—CH($R_g$)CH($R_g$)—, —S—CH($R_g$)CH($R_g$)—, —S(O)—CH($R_g$)CH($R_g$)—, —S(O)$_2$—CH($R_g$)CH($R_g$)—, —NR$_f$—CH($R_g$)CH($R_g$)—, —CH($R_g$)OC(=O)—, or —OCH($R_g$)C(=O)—; wherein each $R_g$ is independently hydrogen, $C_{1-7}$alkyl, aryl, (aryl)$C_{1-7}$alkyl, (aryl)oxy, heteroaryl(oxy), or (aryl)oxy$C_{1-7}$alkyl.

22. The compound of claim 1 wherein X and Y together are —O—CH($R_g$)CH($R_g$)—, —S—CH($R_g$)CH($R_g$)—, —S(O)—CH($R_g$)CH($R_g$)—, —S(O)$_2$—CH($R_g$)CH($R_g$)—, —NR$_f$—CH($R_g$)CH($R_g$)—, —CH($R_g$)OC(=O)—, or —OCH($R_g$)C(=O)—; wherein each $R_g$ is independently hydrogen or $C_{1-7}$alkyl.

23. The compound of claim 1 wherein X and Y together are —O—CH$_2$CH$_2$—.

24. The compound of claim 1 wherein X and Y together are —O—CH($R_g$)CH($R_g$)—, —S—CH($R_g$)CH($R_g$)—, —S(O)—CH($R_g$)CH($R_g$)—, —S(O)$_2$—CH($R_g$)CH($R_g$)—, or —NR$_f$—CH($R_g$)CH($R_g$)—; wherein each $R_g$ is independently hydrogen, $C_{1-7}$alkyl, or together with an $R_g$ on an adjacent carbon atom forms a fused 4, 5, or 6, membered carbocyclic ring.

25. The compound of claim 1 wherein X and Y together are —O—CH($R_g$)CH($R_g$)—, or —S—CH($R_g$)CH($R_g$)—; wherein each $R_g$ is independently hydrogen, $C_{1-7}$alkyl, aryl, or (aryl)$C_{1-7}$alkyl.

26. The compound of claim 1 wherein X and Y together are —O—CH$_2$CH$_2$—, —O—C(CH$_3$)HCH$_2$—, or —S—CH$_2$CH$_2$—.

27. The compound of claim 1 wherein X and Y together are —O—CH$_2$CH$_2$—, —S—CH$_2$CH$_2$—, —S(O)—CH$_2$CH$_2$—, —S(O)$_2$—CH$_2$CH$_2$—, —NR$_f$—CH$_2$CH$_2$—, —CH$_2$OC(=O)—, or —OCH$_2$C(=O)—.

28. The compound of claim 1 wherein R$_2$ is hydrogen.

29. The compound 1,2,8,9,10,11-hexahydro-7H-azepino[4,5-b][1,4]oxazino[2,3,4-hi]indole; or a pharmaceutically acceptable salt thereof.

30. A pharmaceutical composition comprising a compound of claim 28 and a pharmaceutically acceptable excipient.

31. A method for treating anxiety, obesity, depression, schizophrenia, a stress related disease, panic disorder, a phobia, obsessive compulsive disorder, post-traumatic-stress syndrome, immune system depression, a stress induced problem with the gastrointestinal or cardiovascular system, or sexual dysfunction in a mammal comprising administering a therapeutically effective amount of a compound of claim 28 to the mammal.

32. The method of claim 31 wherein the disease is anxiety, obesity, depression, or a stress related disease.

33. The compound of claim 1 wherein R$_2$ is C$_{1-4}$alkyl, C$_{1-4}$alkanoyl, arylcarbonyl, (aryl)C$_{1-2}$alkyl, C$_{1-4}$alkoxycarbonyl, aryloxycarbonyl, arylsulfonyl, or (aryl)methoxycarbonyl, wherein any aryl is optionaly substituted with 1, 2, or 3 substituents independently selected from C$_{1-4}$alkyl and trifluoromethyl.

34. The compound of claim 1 wherein R$_2$ is methyl, ethyl, propyl, isopropyl, acetyl, tert-butoxycarbonyl, benzyloxycarbonyl, benzyl, or p-toluenesulfonyl.

35. A method for preparing a compound of formula (I) as described in claim 1 wherein R$_2$ is hydrogen comprising deprotecting a corresponding compound of formula (I) wherein R$_2$ is benzyloxycarbonyl, or benzyl.

36. The compound:
6-methyl-1,2,8,9,10,11-hexahydro-7H-azepino[4,5-b][1,4]oxazino[2,3,4-hi]indole;
1,2,8,9,10,11-hexahydro-7H-azepino[4,5-b][1,4]oxazino[2,3,4-hi]indole;
6-chloro-1,2,8,9,10,11-hexahydro-7H-azepino[4,5-b][1,4]oxazino[2,3,4-hi]indole;
5-fluoro-1,2,8,9,10,11-hexahydro-7H-azepino[4,5-b][1,4]oxazino[2,3,4-hi]indole;
5-methyl-1,2,8,9,10,11-hexahydro-7H-azepino[4,5-b][1,4]oxazino[2,3,4-hi]indole;
6-fluoro-1,2,8,9,10,11-hexahydro-7H-azepino[4,5-b][1,4]oxazino[2,3,4-hi]indole;
2-methyl-1,2,8,9,10,11-hexahydro-7H-azepino[4,5-b][1,4]oxazino[2,3,4-hi]indole;
1,2,8,9,10,11-hexahydro-7H-azepino[4,5-b][1,4]thiazino[2,3,4-hi]indole;
2,2-dimethyl-1,2,8,9,10,11-hexahydro-7H-azepino[4,5-b][1,4]oxazino[2,3,4-hi]indole;
4-fluoro-1,2,8,9,10,11-hexahydro-7H-azepino[4,5-b][1,4]oxazino[2,3,4-hi]indole;
4-chloro-1,2,8,9,10,11-hexahydro-7H-azepino[4,5-b][1,4]oxazino[2,3,4-hi]indole;
5-chloro-1,2,8,9,10,11-hexahydro-7H-azepino[4,5-b][1,4]oxazino[2,3,4-hi]indole;
6-(trifluoromethyl)-1,2,8,9,20,11-hexahydro-7H-azepino[4,5-b][1,4]oxazino[2,3,4-hi]indole;
5,6-difluoro-1,2,8,9,10,11-hexahydro-7H-azepino[4,5-b][1,4]oxazino[2,3,4-hi]indole;
5-chloro-6-fluoro-1,2,8,9,10,11-hexahydro-7H-azepino[4,5-b][1,4]oxazino[2,3,4-hi]indole;
6-chloro-5-fluoro-1,2,8,9,10,11-hexahydro-7H-azepino[4,5-b][1,4]oxazino[2,3,4-hi]indole;
5,6-dichloro-1,2,8,9,10,11-hexahydro-7H-azepino[4,5-b][1,4]oxazino[2,3,4-hi]indole; or
4,6-dichloro-1,2,8,9,10,11-hexahydro-7H-azepino[4,5-b][1,4]oxazino[2,3,4-hi]indole;
or a pharmaceutically acceptable salt thereof.

37. The compound:
4-bromo-1,2,8,9,10,11-hexahydro-7H-azepino[4,5-b][1,4]oxazino[2,3,4-hi]indole;
5-bromo-1,2,8,9,10,11-hexahydro-7H-azepino[4,5-b][1,4]oxazino[2,3,4-hi]indole;
6-bromo-1,2,8,9,10,11-hexahydro-7H-azepino[4,5-b][1,4]oxazino[2,3,4-hi]indole;
5,6-dibromo-1,2,8,9,10,11-hexahydro-7H-azepino[4,5-b][1,4]oxazino[2,3,4-hi]indole;
4,6-dibromo-1,2,8,9,10,11-hexahydro-7H-azepino[4,5-b][1,4]oxazino[2,3,4-hi]indole;
4-methoxy-1,2,8,9,10,11-hexahydro-7H-azepino[4,5-b][1,4]oxazino[2,3,4-hi]indole;
5-methoxy-1,2,8,9,10,11-hexahydro-7H-azepino[4,5-b][1,4]oxazino[2,3,4-hi]indole;
6-methoxy-1,2,8,9,10,11-hexahydro-7H-azepino[4,5-b][1,4]oxazino[2,3,4-hi]indole;
4-(triflouromethyl)-1,2,8,9,10,11-hexahydro-7H-azepino[4,5-b][1,4]oxazino[2,3,4-hi]indole;
5-(triflouromethyl)-1,2,8,9,10,11-hexahydro-7H-azepino[4,5-b][1,4]oxazino[2,3,4-hi]indole;
4-benzyloxy-1,2,8,9,10,11-hexahydro-7H-azepino[4,5-b][1,4]oxazino[2,3,4-hi]indole;
5-benzyloxy-1,2,8,9,10,11-hexahydro-7H-azepino[4,5-b][1,4]oxazino[2,3,4-hi]indole;
6-benzyloxy-1,2,8,9,10,11-hexahydro-7H-azepino[4,5-b][1,4]oxazino[2,3,4-hi]indole;
4-fluoro-1,2,8,9,10,11-hexahydro-7H-azepino[4,5-b][1,4]thiazino[2,3,4-hi]indole;
5-fluoro-1,2,8,9,10,11-hexahydro-7H-azepino[4,5-b][1,4]thiazino[2,3,4-hi]indole;
6-fluoro-1,2,8,9,10,11-hexahydro-7H-azepino[4,5-b][1,4]thiazino[2,3,4-hi]indole;
4-chloro-1,2,8,9,10,11-hexahydro-7H-azepino[4,5-b][1,4]thiazino[2,3,4-hi]indole;
5-chloro-1,2,8,9,10,11-hexahydro-7H-azepino[4,5-b][1,4]thiazino[2,3,4-hi]indole;
6-chloro-1,2,8,9,10,11-hexahydro-7H-azepino[4,5-b][1,4]thiazino[2,3,4-hi]indole;
4,5-difluoro-1,2,8,9,10,11-hexahydro-7H-azepino[4,5-b][1,4]thiazino[2,3,4-hi]indole;
5,6-difluoro-1,2,8,9,10,11-hexahydro-7H-azepino[4,5-b][1,4]thiazino[2,3,4-hi]indole;
4,6-difluoro-1,2,8,9,10,11-hexahydro-7H-azepino[4,5-b][1,4]thiazino[2,3,4-hi]indole;
4-chloro-5-fluoro-1,2,8,9,10,11-hexahydro-7H-azepino[4,5-b][1,4]thiazino[2,3,4-hi]indole;
4-chloro-6-fluoro-1,2,8,9,10,11-hexahydro-7H-azepino[4,5-b][1,4]thiazino[2,3,4-hi]indole;
5-chloro-6-fluoro-1,2,8,9,10,11-hexahydro-7H-azepino[4,5-b][1,4]thiazino[2,3,4-hi]indole;
6-chloro-5-fluoro-1,2,8,9,10,11-hexahydro-7H-azepino[4,5-b][1,4]thiazino[2,3,4-hi]indole;

4-methyl-1,2,8,9,10,11-hexahydro-7H-azepino[4,5-b][1,4]thiazino[2,3,4-hi]indole;

5-methyl-1,2,8,9,10,11-hexahydro-7H-azepino[4,5-b][1,4]thiazino[2,3,4-hi]indole;

6-methyl-1,2,8,9,10,11-hexahydro-7H-azepino[4,5-b][1,4]thiazino[2,3,4-hi]indole;

4-methoxy-1,2,8,9,10,11-hexahydro-7H-azepino[4,5-b][1,4]thiazino[2,3,4-hi]indole;

5-methoxy-1,2,8,9,10,11-hexahydro-7H-azepino[4,5-b][1,4]thiazino[2,3,4-hi]indole;

6-methoxy-1,2,8,9,10,11-hexahydro-7H-azepino[4,5-b][1,4]thiazino[2,3,4-hi]indole;

4-(triflouromethyl)-1,2,8,9,10,11-hexahydro-7H-azepino[4,5-b][1,4]thiazino[2,3,4-hi]indole;

5-(triflouromethyl)-1,2,8,9,10,11-hexahydro-7H-azepino[4,5-b][1,4]thiazino[2,3,4-hi]indole;

6-(triflouromethyl)-1,2,8,9,10,11-hexahydro-7H-azepino[4,5-b][1,4]thiazino[2,3,4-hi]indole;

4-benzyloxy-1,2,8,9,10,11-hexahydro-7H-azepino[4,5-b][1,4]thiazino[2,3,4-hi]indole;

5-benzyloxy-1,2,8,9,10,13-hexahydro-7H-azepino[4,5-b][1,4]thiazino[2,3,4-hi]indole; or 6-benzyloxy-1,2,8,9,10,11-hexahydro-7H-azepino[4,5-b][1,4]thiazino[2,3,4-hi]indole;

or a pharmaceutically acceptable salt thereof.

38. The compound:

benzyl 2-methyl-1,2,7,8,10,11-hexahydro-9H-azepino[4,5-b][1,4]oxazino[2,3,4-hi]indole-9-carboxylate;

benzyl 2,2-dimethyl-1,2,7,8,10,11-hexahydro-9H-azepino[4,5-b][1,4]oxazino[2,3,4-hi]indole-9-carboxylate;

benzyl 4-fluoro-1,2,7,8,10,11-hexahydro-9H-azepino[4,5-b][1,4]oxazino[2,3,4-hi]indole-9-carboxylate;

benzyl 4-chloro-1,2,7,8,10,11-hexahydro-9H-azepino[4,5-b][1,4]oxazino[2,3,4-hi]indole-9-carboxylate;

benzyl 5-fluoro-1,2,7,8,10,11-hexahydro-9H-azepino[4,5-b][1,4]oxazino[2,3,4-hi]indole-9-carboxylate;

benzyl 5-chloro-1,2,7,8,10,11-hexahydro-9H-azepino[4,5-b][1,4]oxazino[2,3,4-hi]indole-9-carboxylate;

benzyl 5-methyl-1,2,7,8,10,11-hexahydro-9H-azepino[4,5-b][1,4]oxazino[2,3,4-hi]indole-9-carboxylate;

benzyl 6-fluoro-1,2,7,8,10,11-hexahydro-9H-azepino[4,5-b][1,4]oxazino[2,3,4-hi]indole-9-carboxylate;

benzyl 6-chloro-1,2,7,8,10,11-hexahydro-9H-azepino[4,5-b][1,4]oxazino[2,3,4-hi]indole-9-carboxylate;

benzyl 6-methyl-1,2,6b,7,8,10,11,11a-octahydro-9H-azepino[4,5-b][1,4]oxazino[2,3,4-hi]indole-9-carboxylate;

benzyl 6-(trifluoromethyl)-1,2,7,8,10,11-hexahydro-9H-azepino[4,5-b][1,4]oxazino[2,3,4-hi]indole-9-carboxylate;

benzyl 5,6-difluoro-1,2,7,8,10,11-hexahydro-9H-azepino[4,5-b][1,4]oxazino[2,3,4-hi]indole-9-carboxylatebenzyl;

benzyl 5-chloro-6-fluoro-1,2,7,8,10,11-hexahydro-9H-azepino[4,5-b][1,4]oxazino[2,3,4-hi]indole-9-carboxylate;

benzyl 5-fluoro-6-chloro-1,2,7,8,10,11-hexahydro-9H-azepino[4,5-b][1,4]oxazino[2,3,4-hi]indole-9-carboxylate;

benzyl 5,6-dichloro-1,2,7,8,10,11-hexahydro-9H-azepino[4,5-b][1,4]oxazino[2,3,4-hi]indole-9-carboxylate; or benzyl 4,6-dichloro-1,2,7,8,10,11-hexahydro-9H-azepino[4,5-b][1,4]oxazino[2,3,4-hi]indole-9-carboxylate.

* * * * *

UNITED STATES PATENT AND TRADEMARK OFFICE
CERTIFICATE OF CORRECTION

PATENT NO. : 6,407,092 B1
DATED : June 18, 2002
INVENTOR(S) : Kristine E. Frank et al.

It is certified that error appears in the above-identified patent and that said Letters Patent is hereby corrected as shown below:

Title page,
Item [56], References Cited, OTHER PUBLICATIONS, "Martin, J.R., et al.," reference insert -- *The* -- before "*Journal*".

Column 47,
Line 48, insert -- , -- after "wherein".
Line 58, delete "balo" and insert -- halo -- therefor.

Column 48,
Line 7, delete "heteroaryl)" and insert -- (heteroaryl) -- therefor.
Line 36, insert -- aryl, -- after "$C_{1-7}$alkyl,".
Line 52, delete "in" before "independently".

Column 49,
Line 7, delete "($C_{1-7}$alkyl" and insert -- $C_{1-7}$alkl -- therefor.
Line 25, delete "or" and insert -- of -- therefor.
Line 54, delete "(S=)" and insert -- (=S) -- therefor.

Signed and Sealed this

Seventeenth Day of February, 2004

JON W. DUDAS
*Acting Director of the United States Patent and Trademark Office*